(12) United States Patent
Merkin

(10) Patent No.: US 10,372,877 B2
(45) Date of Patent: *Aug. 6, 2019

(54) FILE MANAGEMENT STRUCTURE AND SYSTEM

(71) Applicant: ADVANCED HEALTHCARE SYSTEMS, INC., Houston, TX (US)

(72) Inventor: Richard Merkin, Marina Del Rey, CA (US)

(73) Assignee: ADVANCED HEALTHCARE SYSTEMS, INC., Houston, TX (US)

(*) Notice: Subject to any disclaimer, the term of this patent is extended or adjusted under 35 U.S.C. 154(b) by 26 days.

This patent is subject to a terminal disclaimer.

(21) Appl. No.: 15/239,520

(22) Filed: Aug. 17, 2016

(65) Prior Publication Data

US 2016/0378925 A1 Dec. 29, 2016

Related U.S. Application Data

(60) Division of application No. 13/716,400, filed on Dec. 17, 2012, which is a continuation of application No. 13/712,741, filed on Dec. 12, 2012.

(51) Int. Cl.
*G16H 10/60* (2018.01)
*G06F 19/00* (2018.01)
(Continued)

(52) U.S. Cl.
CPC ............ *G06F 19/324* (2013.01); *G06F 16/21* (2019.01); *G06F 16/22* (2019.01); *G06F 19/00* (2013.01); *G06F 19/325* (2013.01); *G06F 19/3418* (2013.01); *G06Q 10/10* (2013.01); *G06Q 50/22* (2013.01); *G16H 40/63* (2018.01);
(Continued)

(58) Field of Classification Search
CPC ......... G06F 19/322; G06F 19/323–327; G06F 19/00; G06F 19/30; G06F 19/32; G06F 19/324; G06F 19/325; G06F 19/34; G06F 19/3418; G06F 16/21; G06F 16/22; G06Q 50/22; G06Q 50/24; G06Q 10/10; G16H 10/00; G16H 10/60; G16H 40/00; G16H 40/60; G16H 40/63; G16H 40/67;
(Continued)

(56) References Cited

U.S. PATENT DOCUMENTS 5,544,044 A 8/1996 Leatherman
5,902,234 A * 5/1999 Webb .................. A61B 5/0002
600/300
(Continued)

*Primary Examiner* — Jason S Tiedeman
(74) *Attorney, Agent, or Firm* — Stetina Brunda Garred and Brucker

(57) ABSTRACT

The present invention discloses substantially more efficient and effective methods for delivering healthcare whereby patient care can be coordinated effectively and efficiently through changes in different physical settings and levels of care. Coordinated care helps ensure that patients seeking healthcare, and in particular chronically ill patients, with comorbidities get timely care to avoid unnecessary emergency room visits and admissions. Through risk and disease stratification, member profiling, inter disciplinary team follow-up and patient education, the methods of the present invention are operative to effectively allocate available resources, formulate and execute individualized care plans and successfully manage high risk members.

1 Claim, 32 Drawing Sheets

(51) Int. Cl.
*G06F 16/21* (2019.01)
*G06F 16/22* (2019.01)
*G06Q 50/22* (2018.01)
*G06Q 10/10* (2012.01)
*H04L 29/06* (2006.01)
*G16H 40/63* (2018.01)
*G16H 50/30* (2018.01)
*G16H 50/20* (2018.01)

(52) U.S. Cl.
CPC .............. *G16H 50/20* (2018.01); *G16H 50/30* (2018.01); *H04L 63/08* (2013.01); *H04L 63/10* (2013.01)

(58) Field of Classification Search
CPC ........ G16H 50/00; G16H 50/20; G16H 50/30; G16H 80/00; H04L 63/08; H04L 63/10
USPC ............................................. 705/2, 3
See application file for complete search history.

(56) References Cited

U.S. PATENT DOCUMENTS

| | | | |
|---|---|---|---|
| 6,263,330 B1 | 7/2001 | Bessette et al. | |
| 6,283,761 B1 | 9/2001 | Joao | |
| 6,735,569 B1 | 5/2004 | Wizig | |
| 7,251,610 B2 | 7/2007 | Alban et al. | |
| 7,275,220 B2 | 9/2007 | Brummel et al. | |
| 7,464,041 B2 | 12/2008 | Merkin et al. | |
| 7,490,048 B2 | 2/2009 | Joao | |
| 7,533,353 B2 | 5/2009 | Dvorak et al. | |
| 7,657,442 B2 | 2/2010 | Merkin | |
| 7,698,154 B2 | 4/2010 | Marchosky | |
| 7,702,524 B1 | 4/2010 | Whibbs et al. | |
| 7,734,656 B2 | 6/2010 | Bessette et al. | |
| 7,742,930 B1 | 6/2010 | Calhoun, Jr. et al. | |
| 7,801,744 B2 | 9/2010 | Patterson | |
| 7,856,456 B2 | 12/2010 | Bessette | |
| 7,881,950 B2 | 2/2011 | Patterson | |
| 7,899,689 B1 | 3/2011 | Wizig | |
| 7,917,438 B2 | 3/2011 | Kenedy et al. | |
| 7,953,613 B2* | 5/2011 | Gizewski ............. G06F 19/3456 705/3 | |
| 7,984,079 B2 | 7/2011 | Bessette | |
| 8,050,945 B2 | 11/2011 | Patterson | |
| 8,060,376 B2 | 11/2011 | Horner | |
| 8,262,394 B2 | 9/2012 | Walker et al. | |
| 8,285,565 B2 | 10/2012 | Kerr et al. | |
| 8,290,789 B2 | 10/2012 | Wennberg | |
| 8,296,333 B2 | 10/2012 | Bessette | |
| 8,308,062 B1 | 11/2012 | Walton, III | |
| 8,311,855 B2 | 11/2012 | Kerr et al. | |
| 8,321,239 B2 | 11/2012 | Hasan et al. | |
| 8,326,648 B2 | 12/2012 | Kenedy et al. | |
| 8,332,466 B1 | 12/2012 | Cha et al. | |
| 8,335,696 B2 | 12/2012 | Brown | |
| 8,380,631 B2 | 2/2013 | Dala et al. | |
| 8,442,840 B2 | 5/2013 | Menocal et al. | |
| 8,452,617 B2 | 5/2013 | Kerr et al. | |
| 8,762,181 B1 | 6/2014 | Ringold | |
| 2003/0055679 A1* | 3/2003 | Soll ..................... G06F 19/324 705/2 |
| 2005/0010436 A1* | 1/2005 | Merkin ................. G06Q 50/22 705/2 |
| 2005/0010440 A1* | 1/2005 | Merkin ................. G06Q 10/10 705/2 |
| 2005/0091094 A1* | 4/2005 | Wilson ................. G06Q 10/04 705/2 |
| 2006/0190295 A1* | 8/2006 | Merkin ................. G06Q 50/22 705/2 |
| 2006/0235280 A1* | 10/2006 | Vonk .................. G06F 19/3481 600/300 |
| 2006/0277075 A1* | 12/2006 | Salwan ............... G06F 19/3418 705/3 |
| 2007/0122783 A1 | 5/2007 | Habashi | |
| 2007/0214497 A1 | 9/2007 | Montgomery et al. | |
| 2008/0059224 A1 | 3/2008 | Schechter | |
| 2008/0086337 A1 | 4/2008 | Soon-Shiong | |
| 2008/0103369 A1* | 5/2008 | Fabius .................. G06F 19/328 600/300 |
| 2008/0161651 A1 | 7/2008 | Peterson et al. | |
| 2009/0024417 A1 | 1/2009 | Marks et al. | |
| 2009/0080408 A1* | 3/2009 | Natoli .................... H04L 45/00 370/351 |
| 2009/0247834 A1* | 10/2009 | Schechter .............. G16H 50/30 600/300 |
| 2009/0254375 A1 | 10/2009 | Martinez et al. | |
| 2010/0030574 A1* | 2/2010 | Coe ...................... G06F 19/325 705/2 |
| 2010/0106524 A1* | 4/2010 | Wu ....................... G06Q 40/08 705/3 |
| 2010/0131298 A1 | 5/2010 | Buttner et al. | |
| 2010/0131434 A1* | 5/2010 | Magent ................ G06Q 10/06 706/11 |
| 2010/0137693 A1* | 6/2010 | Porras .................... A61M 1/16 600/301 |
| 2010/0217625 A1 | 8/2010 | Dust et al. | |
| 2010/0274589 A1* | 10/2010 | Bauer ............... G06F 17/30914 705/3 |
| 2010/0280851 A1 | 11/2010 | Merkin | |
| 2011/0029321 A1 | 2/2011 | Rourke et al. | |
| 2011/0106565 A1* | 5/2011 | Compton .............. G06Q 50/22 705/3 |
| 2011/0118555 A1* | 5/2011 | Dhumne ................. A61B 5/16 600/300 |
| 2011/0145018 A1 | 6/2011 | Fotsch et al. | |
| 2011/0153448 A1 | 6/2011 | Kerr et al. | |
| 2011/0270632 A1 | 11/2011 | Manning et al. | |
| 2012/0101847 A1* | 4/2012 | Johnson ................ G06Q 10/00 705/3 |
| 2012/0116799 A1* | 5/2012 | Lindskog .............. G16H 50/20 705/2 |
| 2012/0191472 A1 | 7/2012 | Thesman | |
| 2012/0191487 A1 | 7/2012 | Merkin | |
| 2012/0226507 A1 | 9/2012 | Wendt | |
| 2012/0239418 A1* | 9/2012 | Flowers ................ G06Q 50/22 705/2 |
| 2012/0265554 A1* | 10/2012 | Ferguson .............. G06Q 10/10 705/2 |
| 2012/0278094 A1 | 11/2012 | Kovacevic et al. | |
| 2012/0284044 A1 | 11/2012 | Bregante et al. | |
| 2012/0284055 A1 | 11/2012 | Hasan et al. | |
| 2012/0284056 A1 | 11/2012 | Hofstetter | |
| 2012/0284057 A1 | 11/2012 | Hasan et al. | |
| 2012/0290322 A1 | 11/2012 | Bergman et al. | |
| 2012/0296665 A1 | 11/2012 | Merkin | |
| 2012/0303381 A1 | 11/2012 | Bessette | |
| 2012/0329015 A1 | 12/2012 | Thesman | |
| 2013/0030838 A1 | 1/2013 | Myers et al. | |
| 2013/0041690 A1 | 2/2013 | Brough | |
| 2013/0054264 A1 | 2/2013 | Baronov et al. | |
| 2013/0117045 A1* | 5/2013 | Kusens ................. G06Q 50/22 705/3 |
| 2013/0124226 A1 | 5/2013 | Gedala | |
| 2013/0144641 A1 | 6/2013 | Bessette | |
| 2013/0173306 A1* | 7/2013 | Sasidhar ............... G06F 16/951 705/3 |
| 2013/0185087 A1* | 7/2013 | Merkin .................. G06Q 99/00 705/1.1 |
| 2013/0325505 A1 | 12/2013 | Vengco | |
| 2014/0058755 A1* | 2/2014 | Macoviak ............ G06F 19/328 705/3 |
| 2014/0164004 A1 | 6/2014 | Thesman | |
| 2014/0164005 A1 | 6/2014 | Merkin | |
| 2014/0164006 A1 | 6/2014 | Merkin | |
| 2014/0164019 A1 | 6/2014 | Thesman | |
| 2014/0207486 A1* | 7/2014 | Carty ................... G06Q 50/22 705/2 |

\* cited by examiner

FIG. 1

| FIG. 1-1 |
| FIG. 1-2 |

FIG. 1-1

Beneficiary Summary Page — 131

[Search] [Discharge Form] [Complexity Profile] [Care Plan]

Last Name ___ First Name ___ DOB ___ Beneficiary ID ___
Aligned Provider ___ Gender ___ Email ___
Home Phone ___ Mobile Phone ___ Fax ___

Beneficiary Status

Personal Health data Sharing — Opt In ▼
Alcohol & Drug data Sharing — Opt Out ▼

Dual Eligible — No Dual Status ▼

Recommended Program
○ Complex Case Management
○ Disease Management
◉ Self Management
○ Palliative/Hospice Enrolled Date [9/3/2012]   Status [Active]

IDT Team Member Assigned

| Team | Team Member | Date |
| --- | --- | --- |
| Dietician | | 4/20/2012 |
| Case Manager | | 4/20/2012 |
| Aligned Provider | | 4/20/2012 |
| Behavioral Health | | 4/20/2012 |
| Pharmacist | | 4/20/2012 |
| Beneficiary Services | | 4/20/2012 |

Please use the following selections to filter:

From: 1/1/2010
To: 8/27/2012
Status: Not Evaluated

[Filter]

Stratification Criteria (Risk Level)
Tier 1 - weekly follow-up  10 ≤ points
Tier 2 - bi-weekly follow-up  8 ≤ points < 10
Tier 3 - montly follow-up  6 ≤ points < 8
Tier 4 - bi-montly follow-up  4 ≤ points < 6

[Expand Columns]

| Bene ID | Bene Name | Aligned Provider | Total Pts | Tier | Referral Source | Status | Create Date |
|---|---|---|---|---|---|---|---|
| xxxxxxxxx | John Doe #1 | | 12 | 1 | Complex Case Criteria | Not Evaluated | 08/01/2012 |
| xxxxxxxxx | John Doe #2 | | 11 | 1 | Complex Case Criteria | Not Evaluated | 08/01/2012 |
| xxxxxxxxx | John Doe #3 | | 12 | 1 | Complex Case Criteria | Not Evaluated | 08/01/2012 |
| xxxxxxxxx | John Doe #4 | | 21 | 1 | Complex Case Criteria | Not Evaluated | 08/01/2012 |
| xxxxxxxxx | John Doe #5 | | 13.5 | 1 | Complex Case Criteria | Not Evaluated | 08/01/2012 |
| xxxxxxxxx | John Doe #6 | | 11.5 | 1 | Complex Case Criteria | Not Evaluated | 08/01/2012 |
| xxxxxxxxx | John Doe #7 | | 10.5 | 1 | Complex Case Criteria | Not Evaluated | 08/01/2012 |
| xxxxxxxxx | John Doe #8 | | 10 | 1 | Complex Case Criteria | Not Evaluated | 08/01/2012 |
| xxxxxxxxx | John Doe #9 | | 11 | 1 | Complex Case Criteria | Not Evaluated | 08/01/2012 |
| xxxxxxxxx | John Doe #10 | | 14.5 | 1 | Complex Case Criteria | Not Evaluated | 08/01/2012 |

|◀ ◀ 1 2 3 4 5 6 7 8 9 10 - ▶ ▶|  Page size 10 ▼    25891 items in 2590 pages

Beneficiary Trend History
Bene. ID: 015426531

| CreateDate | ClaimsPaidAmountPts | ERAdmissionpts | ERVisitsPts | DiseasePts | TotalPoints | Tier |
|---|---|---|---|---|---|---|
| 05/01/2012 | 3 | 6 | 8.5 | 2 | 19.5 | 1 |
| 05/27/2012 | 3 | 3 | 6.5 | 2 | 14.5 | 1 |

FIG. 2

Hospital Discharge Planning
Evaluation for Complex Case Management

[Beneficiary Profile] [Beneficiary Care Plan]    [Beneficiary Search] [Update]

Last Name                First Name              DOB
Beneficiary ID           Aligned Provider        Date Discharged
Hospital                 Date Admitted           Discharging Hospitals CCM Patient Complexity Profile Class ▶
Code Status    Full Code ▶

Discharge Diagnosis/ Major Procedures

Primary Diagnosis          Septic right knee
Secondary Diagnosis        hx: C spine sz, psychological problems
Major Procedures/ Operations   I & D of advance right knee / arthroscopy Discharge Medication List Viaccezyein gm IV q 2hx 4 wks, Citalepam 40 mg PO q D, Siminatatin 40 mg PO q D, Vicodin 500mg PO PRN<
Nefazodons 200mg POq D, Lamotrigens 150 mg PO q D, Xinex 1 mg PO PRN Discharge Disposition  Home ▶

| FIG. 4-1 |
|---|
| FIG. 4-2 |

FIG. 4-1

Discharge Orders Instruction Appointments

Aligned Provider Appointment

Date & Time [12/10/2010 11:22:00 AM]

Specialty Appointments Follow-up

Name & Specialty

Date & Time [12/10/2010 11:27:00 AM]  Comments [pt states: she needs to make F/U appt X/ Dr. Cohn X 1 wk of D/C 4 aware that referred issues for F/U]

Telephone

Follow-up Testing Radiology Imaging Procedure

Test Procedure  Date & Time [12/10/2010 11:27:00 AM]  Location

Test Procedure  Date & Time [12/10/2010 11:27:00 AM]  Location

Hospital Chart Information Faxed/Forwarded to

Provider [Yes ▼]  Specialist [Yes ▼]  Clinic Case Management Referral Coordinators [Yes ▼]

Home Health Needs

Pt did not want physical therapy on DC

Home Inferior / Outpatient Medications [Yes ▼]

Drug [Vancomycin]  Dose & Frequency [1 qn IV q 2h x 4wk via Picc line]

Duration [4 wks]

Drug  Dose & Frequency

Duration

Alternative Cars

Pallistive Care Agency [No ▼]

Hospice Care Agency [No ▼]

Special Needs / DME has old walker w/ wheels, crutches at home, prior to admit. FWW detected on DC Special Orders Instructions Labs: Vanconycin trough, Chem & on 12/10:10:00 with nursing to do blood draw & wkly with results to Doctor need F/U app in 1 wk of DC w/ Doctor; weekly labs trough, Chem $ Completed by [        ]    Date [12/10/2010 11:29.00 AM]

FIG. 4-2

Complex Case Management
Complexity Profiling (Beneficiary Assessment)

| Discharge Plan | Beneficiary Care Plan | ☐ Beneficiary Declined Assessment | | Update |

Last Name: _____   Firstt Name: _____   DOB: _____
Beneficiary ID: _____   Age: _____   Sex: _____
Admit Date: _____   Aligned Provider: _____

Residence:  ○ SNF    ○ B&C    ○ Assisted Listing    ● Private Home
Age:        ○ <65    ○ 65-85  ○ >85
Number of Critical Events (Hospitalizations / ER visits) in last Six (6) month: [1 ▼]

---

Major organ Systems Dysfunctions

Total Organs Failing [1]
Specific Major organ Dysfuction

| Cardiovascular | _____ [x] | Digestive | _____ [x] |
| Respiratory | _____ [x] | Urinary | _____ [x] |
| Renal | _____ [x] | Infectious Disease | _____ [x] |
| Nervous System | _____ [x] | Endocrine | _____ [x] |
| Hematology Oncology | _____ [x] | Muscloskeletal | HCC 37 - Bone/Joint Muscle Infections / Nect [x] |

FIG. 5

HCC Diagnostic from Actual Data
Cardiovascular
Respiratory
Renal
Nervous System
Hematology Oncology
Digestive
Urinary
Infectious Disease
Endocrine
Muscloskeletal

Total No. of Drug Classification

Drug Classification  ⦿ <4   ○ 4-6   ○ >6

Drug Classification

☐ Aspirin/ Clopidogrel          ☐ Sedatives/ Anxiolytics    ☐ Chemo / Immunosuppressives
☐ NSAIDS                        ☑ Psychotropics             ☐ Anti-Diabetes Meds
☐ Warfarin / Anticoagulants     ☐ Diuretics                 ☑ Antibiotics
☑ Opiates Drug Classifications from bene's actual Rx data ▾
☐ Aspirin/ Clopidogrel          ☐ Sedatives/ Anxiolytics    ☐ Chemo / Immunosuppressives
☐ NSAIDS                        ☐ Psychotropics             ☐ Anti-Diabetes Meds
☐ Warfarin / Anticoagulants     ☐ Diuretics                 ☐ Antibiotics
☐ Opiates

FIG. 6

Functional Status:

General     ○ Good  ● Fair  ○ Poor

Primary Functional Limitation
☐ Dementia    ☐ Psychiatric    ☐ Respiratory    ☐ Cachexia    ☐ Blind
☐ Neurology    ☐ Addiction    ☐ Cardiac    ☐ Musculoskeletal    ☐ Deaf / Mute Vision    [▼]
Hearing    [▼]

Social Support / Careworker Network    ● Good    ○ Fair    ○ Poor
Compliance Level    ○ Good    ● Fair    ○ Poor
Code Status / Advance Directive    ○ DNR / Hospice    ○ Limited Support    ● Full Code

Total Complexity Score

Based on the Complexity Score, recommended Case Program is

Self Management    Complex Case Management    Palliative / Hospice
           ● <12          ○ 13-16          ○ <17

Patient Program [Self Management]      Provider Recommended Program [  ▼]

[Inner Disciplinary Team]     [Coordination of Case]     [Patient Education]
Updated 4/20/2012 11:03:56 AM     Updated     Updated

FIG. 7

Complex Case Management Care Plan

[ Beneficiary Profile ] [ Discharge Form ]   ☐ Complex Case                          [ Update ]

Last Name  [_____]       First Name      [_____]       DOB              [_____]
Beneficiary ID [_____]   Date of Intake  [_____]       Aligned Provider [_____]

Patient Consent:                                          ● Yes  ○ No
Informed regading right to dis-enroll from case mgmt:     ● Yes  ○ No
Patient Responsible Party's Signatures:                   [ verbal consent ]
Primary Reason for Complex Case Management Referral:      [ s/p septic arthritis ]

[ Close All ]

Most recent critical event (Hosp/ER visit) Date and diagnoses    [____] ▦    [ none ▶ ]

Most recent critical event (hospitalization/ER visit) date and diagnoses

● Hospitalization   ○ ER Visit

Date              [ 12/7/2009 ]        Facility    [ AVH ]
Main Diagnoses    [ post-op wound infection ]                    [____] ▦    [ none ▶ ]
Brief Client History [ infected right knee ]

Chronic Medical Conditions
Chronic Medical Conditions

[ colon polyps ]              [ affective disorder ]           [_____]
[ chronic pain syndrome ]     [ agoraphobia ]                  [_____]
[ major depression ]          [ hyperlipidemia ]               [_____]

FIG. 8

| Pain Management & Allergies | | | | |
|---|---|---|---|---|
| Pain Management & Allergies | | | | |
| ▶ | | Allergies | NKDA | none ▶ |
| Medications | | | | |
| Medications | | | | |
| citalopram | | | | none ▶ |
| lamotrigine | | | | |
| nefazolone Hcl | | | | |
| Mental Health Status / Cognitive Functions | | | | |
| Mental Health Status / Cognitive Functions | | | | |
| Normal | ▶ | Depressed | ▶ | Anxious ▶ |
| Restless | ▶ | Listless | ▶ | Somnolent ▶ |
| Comatose / Unresponsive | ▶ | Demented | ▶ | Delirious / Confused ▶ |
| Mild Cognitive Impairment | ▶ | Aphasic | ▶ | |
| Activities of Daily Living | | | | none ▶ |
| Activities of Daily Living | | | | |
| Bathing | Assisted ▶ | Ambulation | Assisted ▶ | |
| Eating | Assisted ▶ | Dressing | Assisted ▶ | |
| Transportation | Assisted ▶ | Toileting | Assisted ▶ | |
| Grooming | Assisted ▶ | | | |
| DME Dependency updates | | | | none ▶ |

FIG. 9

| DME Dependency Updates | |
| --- | --- |
| DME Dependency | |

| Life Planning Activities | ▦ | none ▸ |
| --- | --- | --- |
| Life Planning Activities | | | discussed advance directive

| Cultural and Special Linguistic Needs | ▦ | none ▸ |
| --- | --- | --- |
| Cultural and Special Linguistic Needs | | | needs met

| Caregiver Resources | ▦ | none ▸ |
| --- | --- | --- |
| Caregiver Resources | | |

| Caregiver Relationship | ▸ | Level Of Involvement | |
| --- | --- | --- | --- |
| | | (Hours/Week) | |
| Caregiver First Name | | Phone Number | |
| Caregiver Last Name | | | |

| Community Resources | ▦ | none ▸ |
| --- | --- | --- |
| Community Resources | | |

Please click on the link to find available resources: www.eldercare.gov

| Community Resources | | |
| --- | --- | --- |

| Case management Plans - Short Term | ▦ | none ▸ |
| --- | --- | --- |

FIG. 10

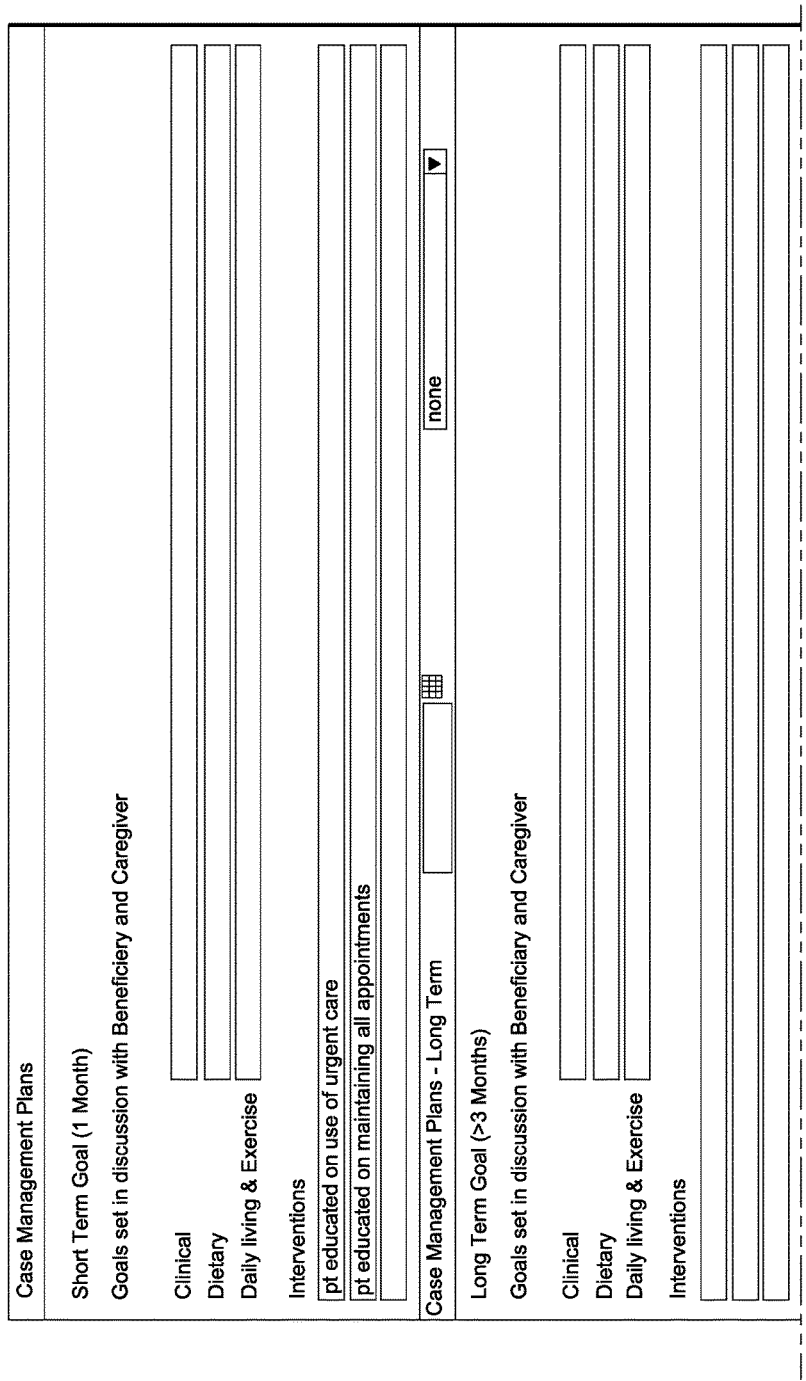

| Follow - up Plans: | | none ▼ |
| --- | --- | --- |
| Follow - up Plans: | | |
| Date | pt to return in 3 wks as soon as results of MRI are available | |
| Date | lab to be repeated | |
| Date | | |
| Potential Barriers to Compliance and Goals | | none ▼ |
| Potential Barriers to Compliance and Goals | | |
| | will depend on disease process | |
| | if pt becomes noncompliant w/ Tx plan | |
| Instructions on Self-Management Plans | | none ▼ |
| Instructions on Self-Management Plans | | |
| Daily Living | consider smoking cessation classes | |
| Health Mgmt | maintain all scheduled appointments | |
| Finance Mgmt | maintain a well balanced diet | |
| Evaluation | | none ▼ |
| Evaluation | | |

FIG. 11-2

| Beneficiary Profile | | | | Submit | Clear |
|---|---|---|---|---|---|
| Beneficiary Name | | Beneficiary ID | | DOB | |

| IDT Provider | Provider Name | Provider ID | Speciality | Last Date assigned |
|---|---|---|---|---|
| Aligned Provider | | | | 04/20/2012 |
| Behavioral Health | | | | 04/20/2012 |
| Specialist 1 | | | | 08/27/2012 |
| Case Manager | | | | 04/20/2012 |
| Dietician | | | | 04/20/2012 |
| Pharmacist | | | | 04/20/2012 |
| Care Giver | | | | |
| Specialist 2 | | | | 08/27/2012 |
| Specialist 3 | | | | |
| Beneficiary Services | | | | 04/20/2012 |

| Ancillary Name | Ancillary ID | Member Count | Member Capacity | Percentage |
|---|---|---|---|---|
| | | | 31000 | 22.9% |
| | | | 31000 | 15.5% |
| | | | 31000 | 11.4% |
| | | | 31000 | 47.1% |

FIG. 13

| Chronic Conditions/Problem List | | |
|---|---|---|
| Education Category | HCC | HCC Description | Last Diagnosed Date |
| Psychiatric Disorder | 55 | Maj, Depressive Bipolar, & Disorders | 6/8/2012 |
| Vascular Disease | 105 | Vascular Disease | 5/1/2009 |
| COPD | 108 | Chronic Obstructive Pulmonary Dis | 12/7/2010 |

FIG. 14

| Surgical History | | |
|---|---|---|
| CPT Code Category | CPT Code | CPT Description | Last Procedure Date |
| Integumentary System | 11056 | Trim Skin Lesion, 2 to 4 | 4/24/2012 12:00:00 AM |
| Nails | 11720 | Debride Nail 1-5 | 5/1/2009 12:00:00 AM |

FIG. 15

Patient Education History

Order | Print | DVD

| Education Category | Education Type | Medium | Language | Material Name | Ordered Date | Ordered By | Completed Date | Completed By |
|---|---|---|---|---|---|---|---|---|
| ☐ Orthopedics and Rheumatology, Sexual Health | After Visit | Document | English | Back Pain and Sex: After Your Visit | 8/27/2012 2:34:30 PM | | ⊞ ⏰ | |

FIG. 16

Patient Specific Education Material Recommmended

| Education Category | Education Type | Medium | Language | Material Name |
|---|---|---|---|---|
| ☐ Orthopedics and Rheumatology, Sexual Health | After Visit | Document | English | Hip Pain and Sex: After Your Visit |
| ☐ Cardiovascular | After Visit | Document | English | Learning About High Blood Pressure |
| ☐ Gastrointestinal, Pre- and Post-Op | After Visit | Document | English | Learning About Rubber Band Ligation for Hemorrhoids |

FIG. 17

Order Additional Materials

| Education Category | Education Type | Medium | Language | Material Name |
|---|---|---|---|---|
| ☐ *Select from list* ▸ | ▸ | ▸ | ▸ | ▸ |

| FIG. 19-1 |
|---|
| FIG. 19-2 |

FIG. 19-1

Disease Management
Member Summary

| Enrollment Call | Member Goal | Submit |

Last Name ▯  First Name ▯  DOB ▯
Member ID ▯  Age ▯  Gender ▯
Aligned Provider ▯  Phone Number ▯  Email ▯

| Criteria | Goal | Latest Value | Latest Date |
|---|---|---|---|
| Disease: Anticoagulation Recommended: N Enrollment: | | | |
| PT_INR | | | |
| Disease: Asthma | | | |
| Systolic EP | | | |

Actions Taken

Patient has been explained about the benefits of eating moderation and the adverse effects that could lead to hospitalization if started to bleed. Discussed diet plan and have patient education materials.

◀ ▶

Follow-up Plans

| Date | IDT Member | Criteria | Abnormal Value | Comments |
|---|---|---|---|---|
| 8/15/2012 | | PT_INR | | |
| | | Beta Blocker | | |
| | | Beta Blocker | | |

Notes

The patient had eaten 2 serving of spinach.

Open Items

| Date | IDT Type | IDT Member | Criteria | Abnormal Value | Comments |
|---|---|---|---|---|---|
| ☐ 8/6/2012 12:00:00 AM | | | PT_INR | 35 | Ask to follow diet plans |

[Complete Button]

FIG. 19-2

Disease Management
Diabetes Enrollment Roster

Expand Columns | Clinical Guidelines - Diabetes

| Bene. ID | Last Name | First Name | Aligned Provider | Complex Case Mgmt Status | Enrollment | DM | Total Points | Last Call Date | Call Result | Call Again Dt. |
|---|---|---|---|---|---|---|---|---|---|---|
| xxxxxxx | LName#1 | FName#1 | | 1- Palliative Hospice | Y | Y | 3 | Enrolled | 8/22/2012 12:00:00 AM | 8/26/2012 12:00:00 AM |
| xxxxxxx | LName#2 | FName#2 | | 1- Enrolled | Y | Y | 3 | Enrolled | 8/16/2012 12:00:00 AM | 8/21/2012 12:00:00 AM |
| xxxxxxx | LName#3 | FName#3 | | 5- Not Evaluated | Y | Y | 4 | Call Again | 8/9/2012 12:00:00 AM | 8/31/2012 12:00:00 AM |
| xxxxxxx | LName#4 | FName#4 | | 5- Not Evaluated | N | Y | 4 | Call Again | 8/9/2012 12:00:00 AM | 8/16/2012 12:00:00 AM |

FIG. 20

Disease Management
Diabetes Enrollment Roster

Expand Columns | Clinical Guidelines - Diabetes

| Bene. ID | Last Name | First Name | Aligned Provider | Complex Case Mgmt Status | Enrollment | DM | DM Point | HgbA1c | HgbA1c Point | LDL | LDL Point | Alpha Glucose Inhibitors | Antidiabetic Combinations | Insulin |
|---|---|---|---|---|---|---|---|---|---|---|---|---|---|---|
| xxxxxx | LName#1 | FName#1 | | 1- Palliative Hospice | Y | Y | 1 | 0 | 0 | 0 | 0 | 0 | 0 | 2 |
| xxxxxx | LName#2 | FName#2 | | 1- Enrolled | | Y | 1 | 5.4 | 0 | 0 | 0 | 0 | 0 | 2 |

FIG. 21

Disease Management Enrollment Call

| Member Goal | Member Summary | Submit |

Last Name: ____  First Name: ____  DOB: ____
Member ID: ____  Age: ____  Gender: ____
PCP: ____  Phone Number: ____  Email: ____

Call Details

Call Date: 8/27/2012
Received By: ____
Call Result: *SELECT from list*
Next Call Date: ____
Notes: ____

Recommended Program

- ☑ Diabetes      ☑ Hypertension    ☐ OSA
- ☐ CAD           ☐ COPD            ☑ Depression
- ☐ CHF           ☐ Asthma          ☑ Anticoagulation

Enrollment Status By Program

- ☐ Diabetes      ☐ Hypertension    ☐ OSA
- ☐ CAD           ☐ COPD            ☐ Depression
- ☐ CHF           ☐ Asthma          ☐ Anticoagulation

Content

Member Consent: ○ Yes ○ No
Informed Regarding right to disenroll?: ○ Yes ○ No
Consent Given By: Brother ▾

Call History

| Date | Call Result | Next Call Date | Notes |
|------|-------------|----------------|-------|

FIG. 22

Disease Management
Beneficiary Specific Goal

[ Enrollment Call ] [ Bene. Summary ] [ Submit ]

Last Name [____]  First Name [____]  DOB [____]

Beneficiary ID [____]  Aligned Provider [____]  Age [____]

Goal

| Criteria | New Goal | Latest Goal | Latest Value | Previous Value |
|---|---|---|---|---|
| HgbA1C | [____] | 8.5 | 9.9 | |
| LDL | [____] | 100 | | 95 |
| Cholesterol | [____] | | | |

FIG. 23

| IDT FName | IDT LName | IDT Type | Member ID | First Name | Last Name | Follow Up Date | Follow Up Criteria | Abnormal Value | Comments | Assigned By | Assigned Date |
|---|---|---|---|---|---|---|---|---|---|---|---|
| | | | xxxxxxxxx | John | Doe | 08/06/2012 | PT_INR | 3.5 | Ask to follow diet plans | | 8/27/2012 2:11:17 PM |
| | | | xxxxxxxxx | John | Doe | 08/06/2012 | PT_INR | | | | 8/27/2012 2:15:54 PM |

Disease Management
Follow Up Roster

FIG. 24

Complex Case Management
Beneficiary Complexity Profile Report & Trend

Categories:
● All  ○ Critical Events  ○ Major Organ System Dysfunction  ○ Pharmacologic Profile  ○ Functional Status  ○ Social Support Caregiver Network  ○ Compliance Level  ○ Code Status/Advance Directive

| Beneficiary ID | Name | Age | Evaluation Score 1st | Evaluation Score 2nd | Evaluation Score 3rd | Evaluation Score 4th | Evaluation Score 5th | Evaluation Score 6th | Evaluation Score 7th |
|---|---|---|---|---|---|---|---|---|---|
| xxxxxxxxx | Name#1 | xx | 7 | 7 | 16 | 18 | 17 | 17 | 0 |
| xxxxxxxxx | Name#2 | xx | 16 | 0 | 0 | 0 | 0 | 0 | 0 |
| xxxxxxxxx | Name#3 | xx | 13 | 13 | 0 | 0 | 0 | 0 | 0 |
| xxxxxxxxx | Name#4 | xx | 0 | 0 | 15 | 15 | 0 | 0 | 0 |
| xxxxxxxxx | Name#5 | xx | 15 | 9 | 9 | 9 | 0 | 0 | 0 |
| xxxxxxxxx | Name#6 | xx | 17 | 16 | 16 | 0 | 0 | 0 | 0 |
| xxxxxxxxx | Name#7 | xx | 2 | 16 | 0 | 4 | 0 | 0 | 0 |
| xxxxxxxxx | Name#8 | xx | 1 | 1 | 0 | 0 | 0 | 0 | 0 |
| xxxxxxxxx | Name#9 | xx | 13 | 15 | 1 | 0 | 0 | 0 | 0 |
| xxxxxxxxx | Name#10 | xx | 1 | 1 | 1 | 4 | 12 | 13 | 13 |

FIG. 25

Complex Case Management
Complexity Score based on entry date

| Beneficiary Info: | Beneficiary ID: 3851125829 | Name: John Doe | Age: 51 | | | | |
|---|---|---|---|---|---|---|---|
| Categories | | 1st | 2nd | 3rd | 4th | 5th | 6th |
| Critical Events | | 2 | 0 | 0 | 0 | 0 | 0 |
| Major Organ Systems Dysfunction | | 1 | 0 | 0 | 0 | 0 | 0 |
| Pharmacologic Profile | | 3 | 0 | 0 | 0 | 0 | 0 |
| Functional Status | | 2 | 0 | 0 | 0 | 0 | 0 |
| Social Support Caregiver Network | | 2 | 0 | 0 | 0 | 0 | 0 |
| Compliance Level | | 2 | 0 | 0 | 0 | 0 | 0 |
| Code Status/Advance Directive | | 3 | 0 | 0 | 0 | 0 | 0 |

FIG. 26

HEALTH RISK ASSESSMENT (HRA) FORM

DEMOGRAPHIC INFORMATION:

Name Case Coordinator or Manager:     Case Coordinator or Manager Contact Number:
Date of this Assessment:     CASE #:

*Answers to the Following Questions Are Per Member or Care Giver Interview Responses:*

| | | | |
|---|---|---|---|
| MEMBER NAME: | LOB :[SELECT ONE ▼] | Would the member/caregiver (CG) like to participate in this program? [SELECT ONE ▼] | |
| Health Plan ID# | SNP Plan :[SELECT ONE ▼] | Member Participation Level: [Select ▼] | |
| DOB/AGE: | Health Plan: [SELECT ONE ▼] | Member has Opted-Out: [Select ▼] | |
| Sex: [SELECT ONE ▼] | WHO Referred to CM:[SELECT ONE ▼] | Member Unable to Contact: [Select ▼] | |
| PCP NAME: | PCP Number: | Case Type: [SELECT ONE ▼] | |
| Contacted:[Select ▼] Date: | Date of Last Office Visit with your PCP: | Date History & Physical Requested from PCP: | |
| Marital Status:[Select ▼] | Language Spoken Primary:[Select ▼] | Language Understood Primary:[Select ▼] | Language Read Primary:[Select ▼] |
| ALLERGIES(if none indicate NKA): | Language Spoken Secondary:[Select ▼] | Language Understood Secondary:[Select ▼] | Language Read Secondary:[Select ▼] |
| WHAT IS YOUR ETHNICITY:[SELECT ONE ▼] | What are your living arrangements/who do you live with? (IF Member is Homeless Refer to Social Worker) (If the answer is HOMELES, address in a care plan and request Social Worker intervention): [SELECT ONE ▼] | | |
| CULTURAL LINGUISTIC NEEDS: [SELECT ONE ▼] | [SELECT ONE ▼] | Other/Needs: N/A | |
| Emergency Contact Person: | Emergency Contact Number: | | |

PSYCHO-SOCIAL STATUS Per Member Interview Responses (Specify using drop down or free boxes)

| | | | |
|---|---|---|---|
| Disease Process: | Disease Process: | Disease Process: | [Drop Box ▼] |
| Member's view of their own health? [Select ▼] | Is member able to manage their own healthcare? [Select ▼] | Does member attend activities outside the home? | [Select ▼] |
| Member's view of their quality of life? [Select ▼] | Who manages member's healthcare? [Select ▼] | Name/number of person who manages healthcare for member: | |
| Member's Cognitive status? [Select ▼] | Is member able to manage their own finances? [Select ▼] | Does member have good psycho-social support system? | [Select ▼] |
| PHQ-2 QUESTIONS: Over the last 2 weeks, have you often been bothered by:(YES to either question, f/u with PHQ-9) | 1. Little interest or pleasure in doing things? [Select One ▼] | 2. Feeling down, depressed, or hopeless? | [Select One ▼] |
| PHQ9 Completed:[Select ▼] Date: | Sent to PCP: [Select ▼] | Date Sent To PCP: (If Blank = N/A) | |

Lifestyle and Life Planning Per Member Interview Responses (Specify using drop down or free boxes):

| | | | |
|---|---|---|---|
| Does the member have any life planning documents in place? [Select ▼] | If life planning is in place, indicate which type of process member has in place [Select ▼] | Request a copy of document for member's file from member | [Select ▼] |
| What is the member's code status? [Select ▼] | Does the member use alcohol? [Select ▼] | Does the member use tobacco? | [Select ▼] |
| Does the member use Marijuana? [Select ▼] | Does the member use any other non-prescribed narcotics? [Select ▼] | Is member sexually active? | [Select ▼] |

CLINICAL CONDITIONS Per Member Interview Responses Does the Member Have now or a history of ANY of the following?
(Specify using drop down or free boxes); Any RED YES answer = 1 point each:

| | | |
|---|---|---|
| Disease Process: [Drop Box ▼] | Disease Process: [Drop Box ▼] | Disease Process: [Drop Box ▼] |

FIG. 27A

| Asthma? | | Schizophrenia? | Select ▼ | CANCER? | Select ▼ |
|---|---|---|---|---|---|
| Emphysema/COPD? | Select ▼ | Anxiety? | YES ▼ | What kind of Cancer? | Select ▼ |
| SOB? | Select ▼ | Alzheimer's or Dementia? | Select ▼ | Chronic Kidney Disease? | Select ▼ |
| Pneumonia? | Select ▼ | Parkinson's? | Select ▼ | End Stage Renal Disease? | Select ▼ |
| Depression? | Select ▼ | Arthritis? | Select ▼ | Is this member on Dialysis? | Select ▼ |
| MI? | Select ▼ | Osteoporosis? | Select ▼ | If on Dialysis, where do they go? | |
| Congestive Heart Failure? | Select ▼ | Diabetes? | Select ▼ | Urinary tract infection? | Select ▼ |
| Irregular HR/Angina? | Select ▼ | Neuropathy? Where? | Select ▼ | HIV/AIDS? | Select ▼ |
| Hypertension (HTN)? Enter last known B/P | Select ▼ | Amputation of a limb? Which Limb? | Select ▼ | Constipation? | Select ▼ |
| Stroke/CVA? | Select ▼ | Retinopathy? | Select ▼ | Diarrhea? | Select ▼ |
| Coronary Artery Disease (CAD)? | Select ▼ | IBS/ULCERATIVE COLITIS/CHRON'S? | Select ▼ | Hepatitis? | |
| Hyperlipidemia? | Select ▼ | GI Bleed? | Select ▼ | Chronic Liver Disease? | |
| Peripheral Artery Disease? | Select ▼ | GERD/ Ulcers? | Select ▼ | Other Issues | |
| Height: Weight: | | BMI by Calculator (www.bmi-calculator.net): | | Is the member Obese? | Select ▼ |
| Does the member have acute or chronic PAIN? | Select ▼ | Where is the PAIN located? | | What is the member's current pain level? | Select ▼ |
| How many medications does the member take daily? | | Is member on Anticoagulation Therapy? | Select ▼ | Does member take pain medication on regular basis? | Select ▼ |
| Checked for polypharmacy issues: | | If so, on an anticoagulation program? | Select ▼ | Had Tetanus shot in the last 10 years? | Select ▼ |
| Has member had a flu shot in the last year? DATE: | Select ▼ | Has member had a Pneumovax shot in the last 5 years? DATE: | Select ▼ | Does member take all medications as ordered by their providers? | Select (If NO 1 pt) |

FIG. 27B

| MEDICATIONS (If NONE Check Here ☐ ): Medications member is currently taking at home, include vitamins and over the counter drugs: Greater than 12 meds chart in notes and notify PharmD/MD: ||||||||
|---|---|---|---|---|---|---|---|
| DRUG NAME | DOSE | How often | DRUG NAME | DOSE | How often | DRUG NAME | DOSE | How often |
| | | | | | | | | |
| | | | | | | | | |
| | | | | | | | | |

| FUNCTIONAL STATUS - Activities of Daily Living Per Member Interview Responses Does The Member Have ANY of the following? (Specify using drop down or free boxes: Any RED answer = 1 point each IF not corrected: (Document in Case notes any issues) |||||
|---|---|---|---|---|
| Visual impairment? | Yes - corrected w/ | Difficulty bathing? | Select ▼ | Incontinent of the bowel? | Select ▼ |
| A hearing impairment? | Select ▼ | Difficulty dressing? | Select ▼ | Incontinent of the bladder? | Select ▼ |
| Speech impairment? That interferes with their ability to communicate? (1pt - if unable to communicate) | Select ▼ | Difficulty transferring from one surface to another? | Select ▼ | Difficulty or unable to prepare meals? | Select ▼ |
| | | Difficulty feeding self? | Select ▼ | Difficulty or unable to do housekeeping? | Select ▼ |
| Any difficulty walking or maintaining their balance? | Select ▼ | Feeding tube? | Select ▼ | Difficulty shopping or buying food? | Select ▼ |
| | | Feeding tube is it old or new? | | Where is the weakness? | Select ▼ |
| Any falls in the last 6 months, how many have they had? | Select ▼ | Weakness of the extremities that interfere with their self care or mobility? | Select ▼ | Assistance or CARE-GIVER? | Select ▼ |
| | | | | If YES, how often? | Select ▼ |
| Device used to ambulate? | Select ▼ | A manual or electric wheelchair or scooter for mobility? | Select ▼ | Is it used for in home mobility or outside? If member uses an electric wheel chair or scooter where did they get it? Select | Select ▼ |
| Was Hospice discussed with this member or the caregiver? | Select ▼ | Was Palliative Care discussed with this member or the caregiver? | Select ▼ | Was a Palliative Care or Hospice evaluation ordered? | Select ▼ |
| Who was Hospice discussed with (name)? | | Who was Palliative Care discussed with (name)? | | If ordered, name and telephone number of agency → | |

FIG. 27C

| ANTICIPATED COMMUNITY RESOURCES/ | |
|---|---|
| TRANSPORTATION ISSUES - Per Member Interview Responses (If NONE Check Here ☐ ): What resources are anticipated to be needed for this member/patient or caregiver to support the member/patient in the community or to coordinate with Medicaid benefits? Any RED answer = 1 point each IF not corrected | |
| Community Resources(anticipated or needed): | Transportation Issues (anticipated or needed): |
| | Does the member have any difficulty getting to and from medical or dental appointments? [Select ▼] |
| | Who transports the member when needed? |
| | Name of person who transports member: |
| | Telephone number of person who transports member: |
| UTILIZATION PATTERNS Per Member Interview Responses "How many Times Has the...": (Specify using drop down or free boxes): Any RED answer > 0 = 1 point each | |
| member been to the ER in the last 3 months? | been admitted to the Hospital in the last 3 months? | been to the Urgent Care in the last 3 months? |
| If went to the ER, called PCP before going? [Select ▼] | If admitted to the Hospital, planned or unplanned? [Select ▼] | Did the member go during PCP Office hours (9am - 5pm)? [Select ▼] |
| # SNF days used in benefit period (if known)? | If planned, what was the admission for? | Were PCP appointments available? [Select ▼] |
| ANTICIPATED INTERDISCIPLINARY CARE TEAM/FOLLOW UP NEEDED: Select all that apply | |
| Participant: Name/#: | Participant: Name/#: |
| Participant: Name/#: | Participant: Name/#: |
| Participant: Name/#: | Participant: Name/#: |
| Other: Name/#: | Other: Name/#: |
| FOLLOW UP APPOINTMENTS CURRENTLY SCHEDULED (If referred upon hospital discharge): | |
| Provider Type [Select ▼] | Name/#: | Date: |
| Provider Type [Select ▼] | Name/#: | Date: |
| Provider Type [Select ▼] | Name/#: | Date: |
| MEMBER UNDERSTANDING AND SATISFACTION PROCESSES Per Member Interview Responses: | |
| Member Satisfaction Survey/EVALUATION OF PROGRAM (TO BE DONE ANNUALLY & WHEN CASE IS CLOSED); CM to send survey | [SELECT ONE ▼] |
| Member or Family/Caregiver understanding of this process and/or program: | [SELECT ONE ▼] |
| Assess for type of participation that can be utilized with the patient and/or the caregiver: | [SELECT ONE ▼] |
| CASE MANAGEMENT ADMISSION SUMMARY (Initial Charting): | |
| INITIAL NOTES BY CASE MANAGER (Indicate here the items/focus that you and the member/caregiver have agreed to focus on for the initial care plan on this member, this will be the basis for admission to the program, be sure to include medication reviewed with the member/caregiver) | |
| SCORING / MEETS CRITERIA? | |
| SNP MEMBERS: Score 0-11 (LOW SNP): place member on Special Needs Program and assign to SNP coordinator once HRA, Care Plan and initial entry completed. | NON SNP MEMBERS: Score 0-11 (LOW CM): Does not meet criteria for Case Management - notify referring provider of outcome/decision. |
| Score 12-18 (Medium SNP): place member on Ambulatory Case Management Program (ACM/SNP) | Score 12-18 (MEDIUM CM): place member on Ambulatory Case Management Program (ACM) |
| Score 19 or higher (HIGH SNP): place member on Comprehensive CM Program (CCM/SNP) | Score 19 or higher (HIGH CM): place member on Comprehensive CM Program (CCM) |
| | Count the points from this form and give total score here: ENTER SCORE MEETS CRITERIA FOR: [SELECT ONE ▼] |
| ACUITY: [SELECT ONE ▼] | |

FIG. 27D

FILE MANAGEMENT STRUCTURE AND SYSTEM

CROSS-REFERENCE TO RELATED APPLICATIONS

The present application is a divisional of U.S. patent application Ser. No. 13/716,400, filed Dec. 17, 2012, entitled HEALTHCARE ADMINISTRATION METHOD FOR COMPLEX CASE AND DISEASE MANAGEMENT, which is a continuation of U.S. patent application Ser. No. 13/712,741, filed Dec. 12, 2012, entitled HEALTHCARE ADMINISTRATION METHOD FOR COMPLEX CASE AND DISEASE MANAGEMENT, all of the teachings of which are incorporated herein by reference.

STATEMENT RE: FEDERALLY SPONSORED RESEARCH/DEVELOPMENT

Not Applicable

BACKGROUND

The main causes for health care spending waste are overtreatment of patients, the failure to coordinate care, and the administrative complexity of the health care system. In this regard, healthcare is typically administered in a piecemeal fashion via a process that is typically initiated by a patient's self-assessment or self-diagnosis. Depending on the individual patient's judgment, the patient will typically seek treatment at a traditional "brick and mortar" facility, whether it be a doctor's office, clinic, hospital/emergency room, or the like. Alternatively, the patient may forego or delay seeking treatment, possibly due to medical ignorance, fear of seeking healthcare, cost constraints or some other factor that in turn causes a medical condition to substantially worsen which could have otherwise been prevented or more easily treated.

To the extent care is ultimately rendered, there is often a disconnect regarding the continuum of care that is administered to a particular patient. In this regard, often times a patient is treated by multiple healthcare providers that are often not in communication with one another and do not have a comprehensive assessment of the patient's condition. For example, a patient may have a regular physician overseeing the medical management of one or more chronic conditions but at the same time intermittently be treated by other healthcare providers for unrelated or acute conditions that may not take into account all of the different health issues affecting that particular patient, such as any medications the patient may be on, the patient's pre-existing health conditions, most recent lab results, and the like.

As such, the delivery of healthcare becomes uncoordinated and causes critical patient data to become fractured and decentralized, and much less considered in its entirety when treatment options are considered. Moreover, because any healthcare that is ultimately delivered is through "brick and mortar" facilities, there is often times an overutilization of healthcare resources, and in particular physician examination time. With respect to the latter, it is well recognized that many office and clinic visits, and especially visits to emergency rooms, are unnecessary, wasteful and add to the expense of healthcare when many times such conditions can be easily addressed in a home-based setting or whereby care is delivered directly to the patient outside of a "brick and mortar" healthcare facility.

The aforementioned problems are exacerbated when multiplied over a large patient population, and in a particular patient population having a significant prevalence of medical conditions that require significant healthcare resources to address. Such chronic, high-maintenance conditions, such as diabetes, cancer, asthma, and heart disease, thus produce patients that are often times no longer treated as individual patients, but rather a patient that falls within a sub-category of high cost, complex disease management.

In the healthcare industry, disease management at such level is typically addressed by stratifying the population (population management) in order to target interventions in the most efficient and cost-effective way. In the population management process, however, there is no focus on treating the patient as a whole. For patients in a specific disease registry, the focus is on achieving clinical goals set at the registry level. The patient is, however, not at the center.

A highly successful disease management program should be designed to set patient-specific goals for one or more comorbidities but at the same time have all the operational efficiencies of population management (i.e., several disease registries based on comorbidities). Such program should further provide for coordinated care amongst all healthcare providers treating a given patient. Ideally, a continuum of care would be provided that prevents the aforementioned drawbacks associated with multiple healthcare providers treating the same yet not having access to medical records and other vital medical information regarding the overall health of a client, and not to mention the most current up-to-date health information that is updated on a periodic basis.

In addition to the foregoing, any such successful disease management program should be operative to conserve resources, and wherever possible minimize the current wasteful practices associated with "brick and mortar" delivery of healthcare. Instead, methods for administering care should provide for home-based healthcare programs that not only ensure that a high-level of quality care is provided but also minimize the utilization of healthcare resources, particularly at "brick and mortar" facilities, that in turn conserves those resources for patients with health conditions that warrant more aggressive levels of care.

BRIEF SUMMARY

The present invention specifically addresses and alleviates the above-identified deficiencies in the art. In this regard, the present invention is directed to healthcare administration methods that are operative to facilitate the coordination of care amongst healthcare providers in administering care to a plurality of patients within a patient population. The present invention further enables critical healthcare information to be readily accessed and is updated on a frequent basis. The methods of the present invention are likewise operative to conserve healthcare resources, and in particular minimize conventional wasteful practices associated with patient-initiated healthcare and utilization of "brick and mortar" facilities, and instead extensively promote home-based healthcare programs and healthcare delivery. Still further, the present invention is operative to more effectively and efficiently treat patients afflicted with complex and costly healthcare conditions to a much greater degree than conventional prior art practices that further ensures that such delivery of healthcare adheres to objective healthcare quality measures.

To that end, the methods of the present invention first defines a specific patient population. Such population will typically comprise individual patient subscribers/members/enrollees who meet necessary qualifications (e.g., age, financial) to receive healthcare benefits under a planned benefit package whereby each patient accesses a healthcare network of healthcare providers and services based upon their clinical needs and in accordance with their benefit coverage, as per conventional practices. For each patient, a central database is provided that aggregates patient healthcare information from a plurality of sources, including previous claims and hospital admissions, pharmacy data, lab work data and results, healthcare providers and healthcare resources available to patients within a given geographic area and each patient's membership/enrollee data, which is updated on a periodic basis. Such information is made available as needed to any and all healthcare providers providing healthcare to a patient so that each such healthcare provider uses the same up-to-date information as is possible.

To the extent any given patient believes in his or her judgment that a given condition warrants treatment, an initial screening process is provided whereby the patient's condition is first assessed remotely by a healthcare provider having authorization authority to determine treatment, and in particular the decision-making authority to allow such patient to be seen at a conventional "brick and mortar" facility. Such screening process is essentially determined by an assessment of the aggregated healthcare data for such patient, coupled with a key-word based interview process whereby the authorizing healthcare provider, in conjunction with the aggregated healthcare data, reviews the patient's specific condition through communicating directly with the patient, whether it be by phone, email, texting, video exchange, or any other mode of communicating well-known in the art.

To the extent practical, any condition in the authorizing healthcare provider's opinion that can be addressed in a home/residence-based manner, is so provided. In this regard, authorization for the patient to be seen at a conventional healthcare facility, such as a physician's office, clinic, or the like, is permitted only to the extent necessary to meet specified healthcare measures necessary to adequately address or adequately commensurate with a given patient's condition as determined by the authorizing healthcare provider.

Such administration of healthcare is likewise applied for all types of medical conditions, from acute conditions to the treatment of chronic conditions that require aggressive management, are medication intensive and/or incur high expense. In this regard, the present invention identifies nine chronic conditions, namely, anticoagulation, asthma, coronary artery disease, congestive heart failure, chronic obstructive pulmonary disease (COPD), depression, diabetes, hypertension and obstructive sleep apnea (OSA), with patients having been diagnosed with one or more such conditions being integrated within one of nine disease registries. Such disease registries are integrated in connection with specific disease management programs of the present invention and have the ability to enroll, track and trend, set individual goals with all the efficiencies and workflow of population management built within the application.

Reports can be generated using the methods herein that are further provided to aid medical managers to manage the patients' long-term and short term progress. The complexity profile trend empowers medical managers to track the patients' health progress over time. The eligibility verification roster provides access to real-time admissions by integrating data from a third-party vendor that covers a wide geographic area which is an invaluable tool in care coordination and discharge planning.

Along those lines, at all points where healthcare is provided, the methods of the present invention are operative to provide a platform of communication whereby all providers of services within the healthcare networks providing healthcare to the patient population can share information on each individual patient in real time. The ability to establish such a foundation of communication permits the coordination of decisions and actions on behalf of the patient and serves to integrate responsibilities and actions of each of the providers around a patient. Care can thus be administered through home-based care, whenever possible, to thus conserve resources while also optimizing patient outcomes, and are exceptionally effective in managing complex, high-cost patient care.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 3 is an exemplary screenshot identifying the major diagnoses and procedures performed during a patient's hospital admission and medical plans following discharge, including a list of medications that patient has been prescribed and any infusion or outpatient medications with corresponding dosage and frequency.

FIG. 4 is a continuation of the hospital discharge planning screenshot of FIG. 3 that further illustrates data that can be incorporated with respect to a patient's follow-up care, including referrals for special needs and durable medical equipment (DME).

FIG. 5 is an exemplary screenshot produced in accordance with the methods of the present invention for profiling a patient within the patient population based on demographic information, emergency room admissions and specific major organ system dysfunction for purposes of determining complex case management.

FIG. 6 is an exemplary screenshot produced in accordance with the present invention that is operative to profile a patient within the patient population based on the total number of drug classifications prescribed to the patient as further part in determining complex case management.

FIG. 7 is an exemplary screenshot produced in accordance with the methods of the present invention that allows for input of a patient's functional status for use in determining a point score indicative of complex case management.

FIG. 8 is an exemplary screenshot produced via the methods of the present invention that is operative to provide a brief clinical history of a patient within a patient population as part of a complex case management plan.

FIG. 9 is an exemplary screenshot of an on-line form produced pursuant to the methods of the present invention for identifying pain medications and an evaluation of mental health status, cognitive impairments of a patient, and daily living activities as part of a complex case management plan.

FIG. 10 is an exemplary screenshot identifying the durable medical equipment need, life planning and activities of a given patient, and identifying specific cultural and linguistic needs, caregiver resources and caregiver contact information as part of a complex case management plan.

FIG. 11 is an exemplary screenshot of an on-line form for providing information related to the evaluation of case management plans, goals and interventions and likely potential barriers to achieving the healthcare management goals of a given patient within the patient population as part of a complex case management plan.

FIG. 13 is an exemplary screenshot identifying outstanding follow-up items for a patient with regard to the patient's healthcare management and for facilitating communication between healthcare providers.

FIG. 14 is an exemplary screenshot identifying chronic conditions and persistent problems for a patient within a patient population.

FIG. 15 is an exemplary screenshot depicting a patient's surgical history.

FIG. 16 is an exemplary screenshot showing the history of any patient educational materials provided to a patient.

FIG. 17 is an exemplary screenshot identifying recommended educational materials to be provided to a patient.

FIG. 18 is an exemplary screenshot indicating what further additional materials should be ordered for a specific patient.

FIG. 19 is an exemplary screenshot depicting a disease management summary page identifying the specific disease registries for a patient, criteria to be monitored, individual goals and related criteria and action items to be accomplished to fulfill those goals.

FIG. 20 is an exemplary screenshot depicting an enrollment page for a specific disease/condition, namely, diabetes for a given patient, wherein the details associated with such page are collapsed.

FIG. 21 is an exemplary screenshot depicting an enrollment page for a specific disease/condition, namely, diabetes for a given patient, wherein the details associated with such page, as depicted in FIG. 20, are expanded.

FIG. 22 is an exemplary screenshot operative to capture data regarding the efforts to enroll a patient into one or more disease programs.

FIG. 23 is an exemplary screenshot depicting an disease management goal page whereby a beneficiary patient's specific goals are set and evaluated.

FIG. 24 is an exemplary screenshot of a follow-up roster that creates a work list for interdisciplinary healthcare team members to provide care for a given patient.

FIG. 25 is an exemplary screenshot depicting a trend report showing a plurality of patients' complexity assessment over a given period of time.

FIG. 26 is an exemplary screenshot produced in accordance with the methods of the present invention operative to provide scores for a variety of categories related to a patient's disease and the management of such disease, as well as the patient's progress.

FIG. 27A is the first page of a four page form for use in determining if a patient meets the criteria for complex care management FIG. 27B is the second page following FIG. 27A of said four page form for use in determining if a patient meets the criteria for complex care management.

FIG. 27C is the third page following FIGS. 27A and 27B of said four page form for use in determining if a patient meets the criteria for complex care management.

FIG. 27D is the last page following FIGS. 27A, 27B, and 27C of said four page form for use in determining if a patient meets the criteria for complex care management.

DETAILED DESCRIPTION

The detailed description set forth below is intended as a description of the presently preferred embodiment of the invention, and is not intended to represent the only form in which the present invention may be implemented or performed. The description sets forth the functions and sequences of steps for practicing the invention for performing novel methods of healthcare administration. It is to be understood, however, that the same or equivalent functions and sequences may be accomplished by different embodiments and that they are also intended to be encompassed within the scope of the invention.

Figures 1, 2:
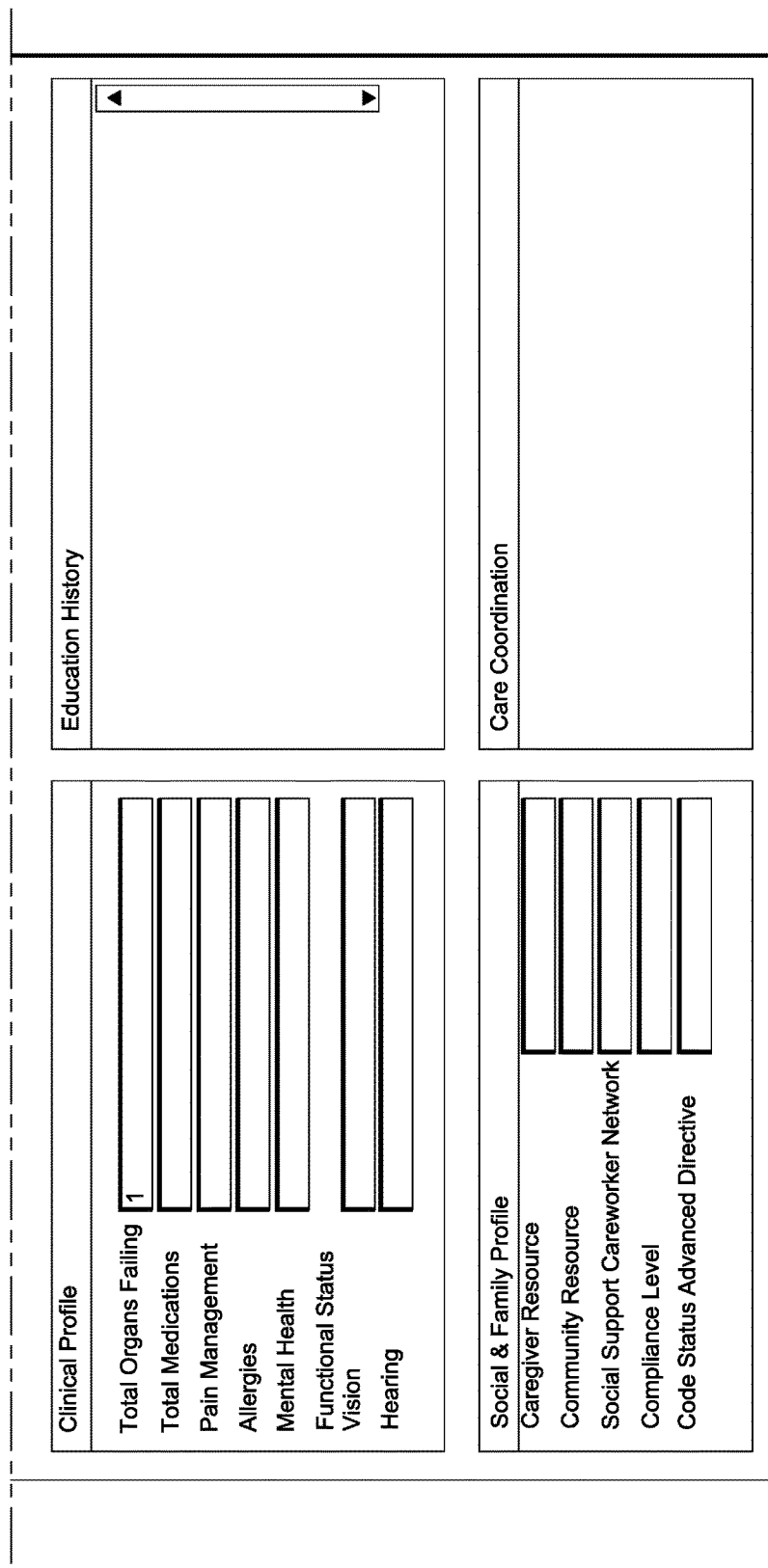
FIG. 1 is an exemplary screenshot of a beneficiary summary page that provides a general overview of the healthcare information associated with a patient operative to receive healthcare benefits according to the methods of the present invention.
FIG. 2 is an exemplary screenshot operative to track a patient's progress as assessed via a historic point trend as per the teachings of the present invention.
Figure 1A:
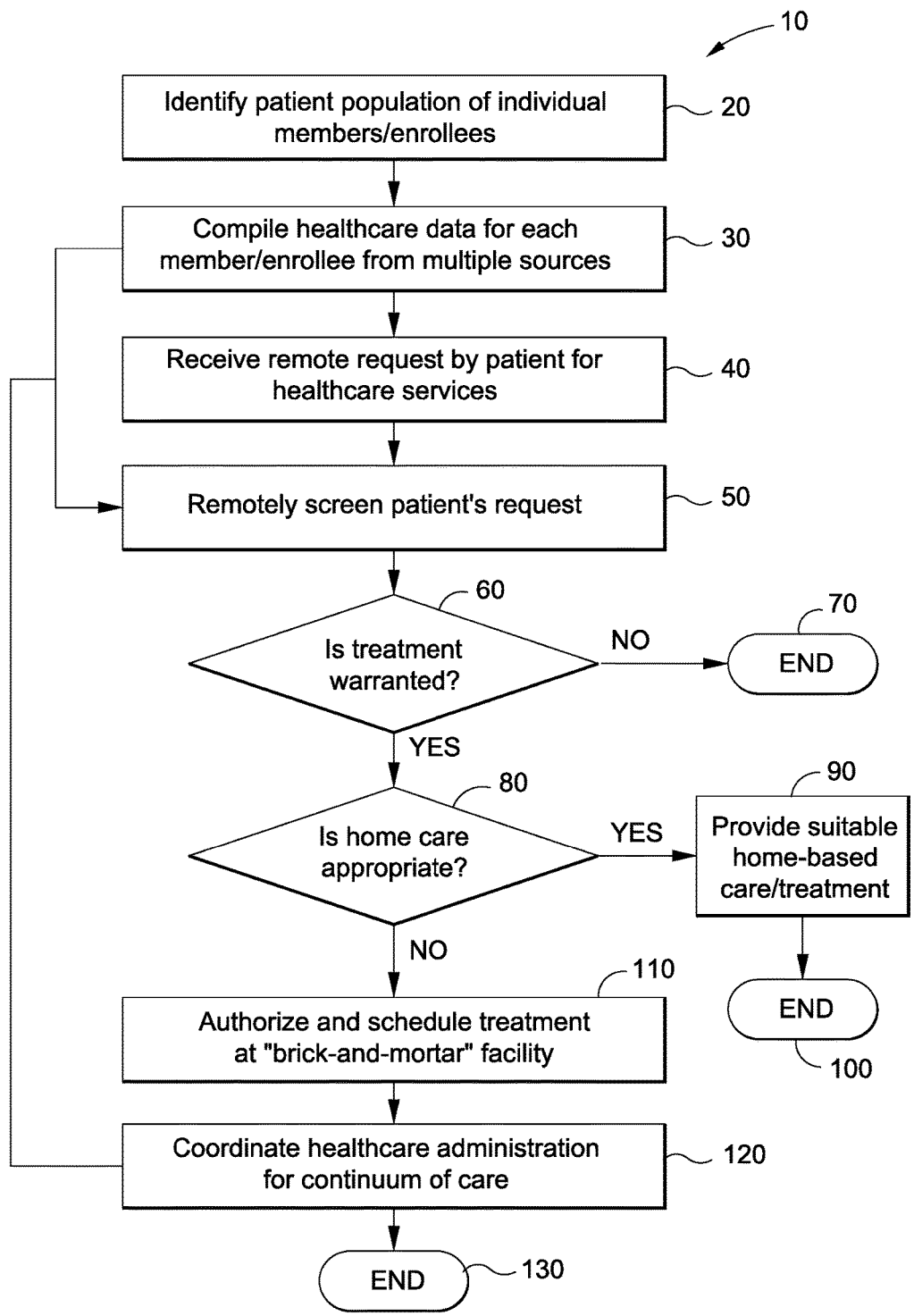
FIG. 1A is a schematic diagram showing a flow chart of the steps for generally performing the healthcare administration methods of the present invention according to a preferred embodiment.
Figure 12:
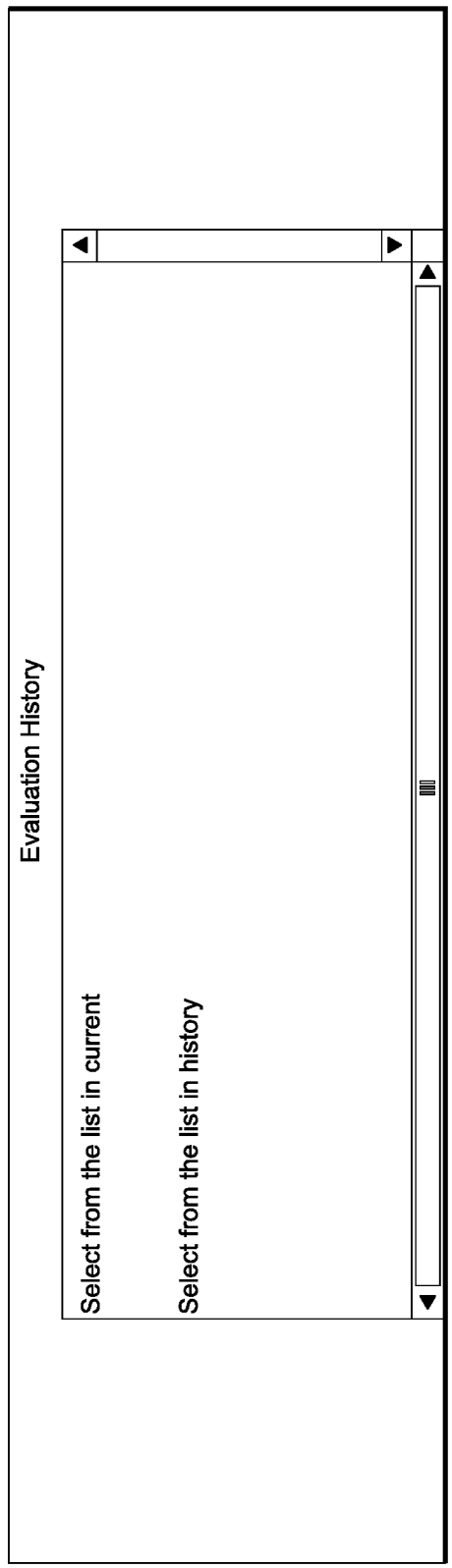
FIG. 12 is an exemplary screenshot depicting a care plan evaluation and history for a given patient.

Referring now to the drawings, and initially to FIG. 1A, there is shown a flow chart depicting the general steps for performing certain novel methods for administering healthcare to a specific patient population that is operative to provide substantially more effective and efficient healthcare than prior art practices, particularly with respect to patients having complex and/or chronic health conditions. As illustrated, the method 10 comprises the initial step 20 of defining a patient population. Such patient population may be generated by any of a variety of techniques well-known in the art, and will typically utilize conventional patient-subscriber mechanisms, such as patient-subscribers to an insurance plan, frequently referred to in the art as enrollees.

Such patient population is thus provided with the care benefits under the methods of the present invention whereby they access healthcare administering networks and providers and services based upon their clinical needs and in accordance with their benefit coverage. As will be readily apparent to those skilled in the art, exemplars of such patients may include employees of employers, including the dependents of the enrollees; independent single enrollees/members, with or without their dependents, who are not employees of employers; beneficiaries of state and federally sponsored insurance coverage, namely, Medicaid and Medicare beneficiaries who meet certain age and financial qualifications to receive insurance; and enrollees whose qualifications permit them coverage through both state and federal programs and have Medicaid and Medicare coverage.

Once such patient population has been identified, an aggregation of medical data compiled from multiple sources of healthcare data are compiled within a central database 30 and made available to the various healthcare providing entities that will provide care to the patient population. Such data comes from multiple sources and, unlike prior art methods, is updated on a frequent basis so as to always provide the most up-to-date medical information about a given patient within the patient population so that all such information is centralized. Such data is comprised of aggregated and detailed data from the following sources set forth in Table 1.

TABLE 1

| # | Data Type | Source | Information Extracted | Frequency |
|---|---|---|---|---|
| 1 | Claims | Centers for Medicare/Medicaid Service (CMS) Claims Data and Electronic Medical Records (EMR) Claims Data | Claim at the member level and aggregate paid amounts, ER visits, admissions | Monthly |
| 2 | Membership | CMS Eligibility Data | Member details | Monthly |
| 3 | Providers | CMS Provider Dat | Provider details including geography | Monthly |
| 4 | Utilization | 3$^{rd}$ Party Vendor | Potential admissions and utilization data | Real-time |
| 5 | Patient Education | 3$^{rd}$ Party Vendor | Prescriptive patient education material | As required |
| 6 | Pharmacy | CMS Pharmacy data | Member pharmacy details | Monthly |
| 7 | Lab | 3$^{rd}$ Party Vendor (e.g., Quest/LabCorp) | Member lab details | Weekly |

As will be readily understood by those skilled in the art, sources of data from which the various data are derived can be readily accessed through commercial software and data bases practiced in the art. For example, information derived from claims, membership, providers and utilization can be derived from any of a variety of health plan administration software, including the EZ-CAP® software produced by MZI HealthCare, LLC of Valencia, Calif. Likewise, lab results can be readily accessed through third party diagnostic testing providers such as LabCorp Laboratory Corporation of America and Quest Diagnostics. Other sources of data that can be accessed for providing comprehensive patient healthcare information will further be readily appreciated by those skilled in the art.

The computer/server architecture necessary for such information to be aggregated, stored and updated may be accomplished by a variety of conventional hardware known in the art. Exemplary of such hardware includes MicroSoft SQL Server 2005 or 2008. Other system hardware and conventional telecommunications technology will be readily apparent to those skilled in the art. In this regard, it is believed that all of the data identified in Table 1 and the sources from which they are derived are well-known and readily accessible using conventional telecommunications technology.

Once this information is compiled in step 30, healthcare is administered to the patients within the patient population through a healthcare network. As is well-known and practiced in the art, healthcare networks comprise medical facilities, such as hospitals, skilled nursing facilities, free standing surgery centers, dialysis centers, urgent care centers, facilities for performing radiology, laboratory facilities and the like. Such healthcare networks further include healthcare providers such as primary care and specialty physicians, administrative management personnel such as physicians directors, case managers, coordinators, custom service personnel, provider relations, contracting personnel, finance personnel, personnel for paying claims, authorization and quality programs and the managers that oversee them, health education services and related support personnel. The present invention further envisions the healthcare network comprising community and home-based services such as home health nursing, palliative and hospice services, social/respite services, transportation services, volunteer services, home-based medical equipment and pharmacist-controlled medication management services. It will further be appreciated that for all such entities and personnel, each will be credentialed in accordance with state and federal licensure standards.

The administration of healthcare, in its most general sense, will be initiated at step 40 whereby a patient within the patient population makes a request for healthcare services. The methods of the present invention, however, contemplate that such request for services will not be through conventional patient-initiated actions to seek out and utilize, in the patient's discretion, whatever resources may be made available in the healthcare network, but instead will be subject to a remote screening process as set forth in step 50. As contemplated, such screening will involve direct communication between the patient explaining his or her specific condition with a healthcare provider having the requisite knowledge and training to assess the patient and will further have the authorization necessary to permit the patient to receive whatever treatment may be necessary for the patient's specific condition.

In making such assessment, the authorizing agent performing the screening function in step 50 may use any of a variety of conventional diagnostic screening techniques so as to assess the patient's specific condition remotely. As will be appreciated by those skilled in the art, such assessment will be made typically through any of a variety of telecommunications modalities, such as through a phone interview, texting, email, instant messaging, video conferencing and the like.

While a variety of diagnostic tools may be deployed, the present invention expressly contemplates at least two primary factors being taken into consideration in determining whether treatment for a given condition should be provided, and if so to what degree. Specifically, the authorizing healthcare provider will take into consideration the aggregated healthcare data compiled in step 30 so as to be given the most recent medical information and history associated with the patient seeking medical treatment. The authorizing healthcare provider will further make a probative assessment of the patient whereby verbal and/or visual feedback from the patient will be assessed for trigger keywords/symptoms. Although any of a variety of words and/or demonstrated symptoms may trigger the authorizing healthcare provider to initiate the delivery of healthcare, discussed more fully below, certain keywords will typically be recognized as universally requiring the implementation of healthcare. Such words include, for example, "depression," "fever," "chest pain," "dizziness," and the like. Moreover, certain mental disorders will further be screened and keywords such as "suicide" and "alone" will likewise be operative to cause the authorizing healthcare provider to immediately implement applicable action to address a given condition.

Based upon such information, a determination is made in step 60 as to whether or not treatment for a given condition is warranted. In this respect, the decision as to whether or not to provide treatment is made remotely with the patient likewise being in a home/residence environment without the patient already being present at a given healthcare facility.

To ensure that the decision to provide treatment is properly considered, the present invention contemplates the use of consultation with physicians demonstrating the best practice of care and quality outcomes, coupled with the knowledge of the healthcare facilities and resources available to the patient within the patient population that adhere to such quality outcome standards, as well as cost and contract information to ensure that cost-effective options are fully considered in delivering healthcare. Along those lines, it is contemplated that an objective set of medical metrics and quality standards may be utilized in making the assessment in step 60 as to what type of care to render. Exemplary of such standards include the CMS Five-star Quality Rating System; National Committee for Quality Assurance (NCQA) standards including the Healthcare Effectiveness Data and Information Set (HEDIS) quality measures; or Integrated Health Associations (IHA) healthcare pay for performance (P4) program. Such decision making will further preferably take into account potential action alerts, such as home electronic devices that measure certain biological metrics such as blood sugar, as well as whether or not a certain condition is likely to result in the patient being admitted into a hospital within a certain prescribed time in the future. Assessment is further made of any clinical factors that, when combined, show the patient to be at high risk of resulting in further deterioration of a specific clinical condition.

To the extent the decision made at step 60 results in the determination that treatment is not necessary, particularly insofar as a given condition will most likely improve without the need for any type of healthcare, office visit, or the like, the patient is not afforded the opportunity to proceed to consume resources within the healthcare network and the process ends at step 70.

Alternatively, to the extent treatment is warranted, a further decision is made in step 80 as to whether or not the particular condition being addressed can be managed in a home/residential setting. In this regard, the medical home concept of care is the provision of care management and on site clinical services to patient subscribers in a home setting. Services are provided in a coordinated fashion between all providers of services, to the extent warranted, and typically at the request of the physician primarily responsible for attending to the needs of the patient. The goal of the medical home is to avoid higher cost settings for services that can be provided in the home and to prevent unnecessary admissions to these settings, thereby reducing the costs of care for the healthcare network and patient alike, and allowing patients the comfort of their home and the ability to age in place. To the extent a home-based option is available, the same is provided at step 90 and treatment is fulfilled at end 100.

As for the type of healthcare that may be delivered in such setting, the same would adhere to objective quality standards as is recognized by those skilled in the art. As discussed above, such standards include the five-star quality rating system derived by the Centers for Medicare and Medicaid Services (CMS), the Healthcare Effectiveness Data and Information Set (HEDIS) quality measures, and the like. Accordingly, while such healthcare may be administered in a home setting as opposed to a conventional "brick and mortar" facility, no compromise is made to the ultimate care provided to the patient.

Moreover, where appropriate, such treatment provided in step 90 may be the result of a care substitution based on the medical needs and financial considerations of a given patient that may result in better outcomes and higher patient satisfaction. In this regard, care substitutions allow for the selection of services by experts experienced in the best clinical methods of care delivery and contractual arrangements that govern the delivery of care and the services available for that. Care substitutions are critical considerations as to whether care can and should be delivered in home versus medical facility settings, in community offices versus institutional settings. Care substitutions play an important role in patient cohorts under management that are accustomed to obtaining care in high cost settings where the same clinical outcomes could be achieved in lower cost settings.

To the extent a home-based care/treatment is not available, the authorizing healthcare provider will, to the extent necessary in the provider's judgment, authorize and schedule treatment outside of the home/residence environment and in a facility within the healthcare network at step 110. In such instances, the authorization request is reviewed for clinical appropriateness and medical necessity by a management team and accepted or denied or modified in the scope of the request. Authorization approval is forwarded as appropriate, such as to the primary care physician, the provider of the service requested and the patient. In as much as other providers of services will be required to ensure the patient's optimum clinical outcome, the same authorization permission is issued by the management team to each provider of services.

To ensure that the ultimate quality of care is afforded to the patient, the delivery of healthcare that is provided to the patient by the best and most appropriate resources available within the healthcare network and further delivered in such a manner that the patient's condition is comprehensively assessed and treated at step 120. To that end, clinical teams that specialize in the specific stage of the patients care continuum are deployed by network managers to provide services specifically designed to manage that particular stage in the patients care. Management teams comprise in its general format, physicians, licensed nurse case managers, and coordinators, all of whom have access to the use of clinical vendors, services and facilities. As an example, separate clinical management teams are designated to oversee patient care in the hospital or the skilled nursing facility or the home setting or in the community when patients require urgent services that otherwise can be rendered outside an emergency room setting. Other management teams are structured to respond to urgent requests from patients who are deemed complex care patients in need of a higher level of resource and care management, discussed more fully below. Options available to these management teams include immediate access to providers skilled in complex care management, assigned case managers to patients granting patients 24 hour access to care managers and their supervising physicians. Coordination of information and decisions is shared among and between these clinical teams so that patients receive care in a seamless fashion per 120 in FIG. 1A. After treatment is rendered, the process ends at 130.

Complex Case Management

In addition to the aforementioned application to patient-initiated requests for healthcare that are subsequently screened, approved or denied, administered in a home environment or otherwise, so too can such methodology be deployed in complex case management. In this regard, while the management of such cases is obviously more difficult to treat and requires substantially more time and resources to effectively manage, the general principals discussed above and the options they provide in terms of home-based care, care substitutions and care where the patient shares responsibility in the outcome are all taken into consideration for the management of certain conditions that are universally understood to be costly and difficult to manage.

To that end, the present invention's complex case management (CCM) program, as embodied through exemplary computer screenshots set forth in FIGS. 1 and 2-26, utilizes a comprehensive workflow to identify, profile, enroll, treat, follow-up and reassess the care of a patient to achieve the highest level of coordinated care as part of the aggregation and updating of data and care administered to such patients.

Initially, a roster is used to stratify the patient population based on risk level. It is generated using a wide array of data including claims, utilization, and diagnosis as would be compiled per step 30 of FIG. 1A. The high risk patients are then profiled to categorize them into one of three categories (self-management, complex case management and palliative/hospice) via the use of forms and questionnaires such as those depicted in FIGS. 5-7 discussed below. Patients identified as complex case management are then enrolled into the program and a care plan is formulated that is custom tailored to the patient's specific condition that will provide goals, education materials and appropriate IDT follow-up to achieve the best care for the patient's well-being.

To that end, the present invention provides via its computer interface with users a Complex Case Summary Page that provides a general overview of the beneficiary. As shown in FIG. 1 there is illustrated a sample of a CCM Beneficiary Summary form 130 that can be generated per the data compiled in step 30 of FIG. 1A. Such form shows the demographics, contact information and data sharing status. It lists the recommended Complexity program based on the latest profiling or the disease management enrollment, as applicable, with the program enrollment date and current status of enrollment. It provides a brief clinical summary showing the number of organ failures, medications, pain management severity, known allergies and general well-being and cognitive function status. The interdisciplinary team assignment section, discussed below, lists the care providers assigned to the beneficiary with the date of assignment. The social and family profile lists the social support, caregiver resources and community resources applicable to the beneficiary to enhance treatment and care in the home setting. Education history gives a list of patient education material imparted to the beneficiary. The summary page also provides easy access to beneficiary's hospital discharge, complexity profile and care plan.

Complex Case Management Roster

The complex case management roster is a tool used to stratify the patient population based on risk level, per step 30, it is generated using a wide array of data consisting of claims (including diagnoses), utilization, eligibility, and is updated on a regular basis.

The complex case management roster is built on the concept of a point system discussed more fully below where higher number of points indicates a higher acuity/risk level for the patient. As a general rule for purposes of practicing the present invention, a case will generally be deemed complex to the extent the patient has more than two chronic medical conditions selected from the group consisting of asthma, depression, dementia, congestive heart failure, chronic obstructive pulmonary disease, diabetes, obesity, AIDS/HIV, anticoagulation, hypertension, peripheral artery disease, coronary artery disease, end-stage renal disease, chronic kidney disease, and wound problems. Any of a variety of chronic medical conditions known in the art may also be indicators of a complex case. In addition to at least two chronic medical conditions, complex case management may further require that the patient have one high risk criteria, such as poor social support, poor psychological condition, poor functional status, substance abuse, which may either be addiction to alcohol, tobacco use or non-compliance, poor nutritional status or two or more hospitalizations or three or more emergency room visits in the preceding twelve months. As an alternative to the aforementioned high risk criteria, the patient would have one poorly controlled chronic medical condition or two other high risk criteria as established by CMS and/or NCQA, as will be understood by those skilled in the art. In this regard, such high risk assessment includes an evaluation of the patient's health status, including all disease and conditions in hearing or visual impairment; clinical history, including medications, allergies, mental health status, including cognitive function; life-planning activities; activities of daily living; cultural and linguistic needs, preferences or limitations; care-giver resources; available health and dental benefits; spiritual preferences; and living arrangements and transportation issues.

As will be appreciated by those skilled in the art, such assessment may be made via face-to-face interviews, telephonic interviews, or correspondence via email, mail or other conventional forms of communication. It is also contemplated that forms may be utilized to obtain such information, such as that depicted in FIGS. 27A-D.

Complexity Profile

In all other cases, the present invention contemplates designating each patient with a complexity/acuity score and risk stratification. In this regard, patient members/enrollees are scored based upon criteria that is gathered from the patient, and in particular the medical forms of FIGS. 5-7.

In a preferred embodiment, scores based on various criteria are assigned and a specific program for enrollment is recommended.

The scoring system as utilized by the present invention assigns points based on the following:
  Demographic information and type of residence includes patient's age and sex together with current residence whether Home, Assisted Living, SNF, Board and Care facilities etc.
  Total number of ER admissions/visits or Hospitalization in the last six months
  Specific major organ system dysfunction which includes Cardiovascular, respiratory, Renal, Nervous System, Hematology/Oncology, Digestive, Urinary, Infectious Disease, Endocrine and Musculoskeletal. FIG. 5 depicts a sample of such assessment.
  Total number of drug classifications (See FIG. 6)
  Overall Functional Status and Functional Limitations
  Social Support or Caregiver network
  Applicable Code Status/Advanced Directive
  Based on the above criteria, the total points are calculated and the appropriate care program is recommended as following:

a. Self-Management (Score<=12)
b. Complex Case Management (Score 13-16)
c. Palliative/Hospice (Score=>17)

A care coordinator, in collaboration with the physician, has the option to override the recommended program with an appropriate care program to the extent warranted in the physician's judgment. (See FIG. 7)

Patient profiling may be done prior to hospitalization, during an admission or as a part of the discharge process with the help of available medical records or a face to face interaction with the patients, all of which are documented and compiled as part of each patient's aggregation of data. In order to improve the accuracy of the patient's profile, it recommends the diagnoses codes and drugs from patient's actual claims and pharmacy claims for reference. Overall, profiling a patient helps provide an understanding of all aspects of patient's physical, clinical and social situation and develop a personalized care plan as needed.

Specifically, by utilizing the standardized forms, a score is achieved by counting one point for each affirmative or "yes" answer in response to a specific question about a patient's particular medical condition. The points are ultimately added up to provide a final score and the score is then used to determine what program the member should be enrolled in, as well as the level of intervention for the follow-up contact.

Ultimately, a health risk assessment score is assigned that, in turn, determines the particular group the patient will be assigned. According to a preferred embodiment of the present invention, a score of 0-12 would categorize the patient within self-management category; a score of 13-16 in the complex case management category; and a score of 19 or higher within the palliative/hospice category.

Such criteria were selected in generating the roster due to the fact that claims cost and hospital utilization have traditionally been strong indicators for future utilization of emergency healthcare services. Therefore, the stratification of the patient population through this tool enables an organization to accurately assess where the dedication of additional resources for care management would yield the maximum value, which in turn affects what treatment/management is ultimately authorized. For such application, a rolling 15 month timeframe (12 months with a 3 month lag to ensure the completeness of claims data) is applied to the determination of a patient's point tally, and therefore their risk level.

Since the roster displays each patient's point tally based on the most recent claims and utilization data, there is thus designed a feature which allows administrators to track a patient's progress by viewing their monthly historic point trend, broken down by the above-mentioned identification criteria, as can be shown in the exemplary screenshot of FIG. 2.

Hospital Discharge

The Hospital Discharge process is a significant part of the overall care plan and is a factor important in documenting patient data, authorizing further procedures/hospitalizations and in providing a continuum of care through the methods of the present invention. Specifically, the hospital discharge planning checklist provides a tool to eliminate the lack of consistency in both the process and quality of discharge planning across various facilities, thus reducing the hospital bed days, possible readmissions and post-discharge medical costs.

The checklist helps capture the suitable level of care a patient may need during a discharge, whether the patient is discharged to home, a skilled nursing facility, home health care, palliative care or hospice. It helps identify and arrange the necessary support and care from the available community resources and improve the coordination of services following a hospital stay. It captures the major diagnoses and the procedures performed during the admission, a list of medications that a patient is on or has been prescribed, any home infusion or outpatient medications with the dosage and frequency as shown in FIG. 3. Again, such continuum of care is operative to extend from conventional "brick and mortar" facilities, in this case hospitals, whereby such care will transition to a home-based care/treatment for the patient.

Such functioning can also be used to record the follow up appointments with the other healthcare providers, such as the primary care physician and/or a specialist, or appointments for any follow-up testing, radiology, imaging or other procedures. In addition, referrals for special needs, Durable Medical Equipment (DME), etc. can be recorded. An exemplary screenshot of such form as generated through the invention's computer processes is depicted in FIG. 4.

Care Plan

Based on the complexity assessment of a patient, the patient's designated or aligned provider, or the interdisciplinary team comprising specialists, case managers, pharmacists etc., design a care plan that is operative to take numerous factors into consideration and operative to implement a strategy of caring for a patient that can utilize a combination of home-based care/treatment, with the patient taking a significant role in disease management, as well as traditional healthcare treatment, procedures and the like made available through the healthcare network. In this regard, the care plan goes beyond the traditional disease-oriented approach and takes a holistic approach of patient's health and social well-being. It addresses various factors by defining goals for each dimension, assigns specific roles and responsibilities to the patient and the interdisciplinary team members. The overall purpose of developing a care plan is to work collaboratively to understand and address to patient's needs and requirements, to come up with preventive measures and further coordinating care and services. Developing a care plan takes the following into account which, again, is encompassed within the data compiled for each respective patient:

Brief clinical history of the patient which includes the most recent ER visit or hospitalization, major diagnoses pertaining to that admission, any reported chronic medical conditions. Exemplary screenshots shown in FIG. 8.

Severity of pain management, known allergies and drug classifications

Evaluation of mental health status, identifying cognitive impairments and the ease to perform the daily living activities like bathing, transportation, eating etc. (See FIG. 9).

Home and Community Environmental Factors

Still further, in order to address various factors associated with a particular patient's specific home-environment and how such specific living situation may impact the ability to deliver care, particularly with respect to suitable home-based care/treatment, these further factors are taken into consideration, which are documented and made accessible to the central database:

Durable Medical Equipment (DME) dependencies (See FIG. 10)
  Life Planning Activities (See FIG. 10)
  Identify any linguistic and cultural needs, preferences or limitations (See FIG. 10)
  Evaluate the available caregiver resources and the level of involvement (See FIG. 10)
  Available community resources (See FIG. 10)
  Evaluate case management plans, goals and interventions and identify potential barriers to achieve these goals which include factors such as poor compliance to recommended plans, patient disagreement, and need of additional support or even financial hardships (See FIG. 11).
  Care Plan evaluation history (See FIG. 12).

Interdisciplinary Team (IDT)

The healthcare administration methods herein consistently promote an interdisciplinary approach to patient care, as users are able to assign specific IDT providers and involve them in the patients' care through a structured and automated workflow, as discussed above.

Following each patient's IDT provider assignment, the workflow is coordinated through the IDT and patient specific follow-up logs. The follow-up logs are integrated with the computer interface and, provide the users with a single destination incorporating all their assigned patients' outstanding follow-up items pertaining to complex case management, disease management, patient education, outstanding quality measures, provider/patient communication, and documentation management.

This allows the IDT provider to organize, prioritize, and effectively manage their time and resources by focusing on key tasks pertaining to patient care coordination in a systematic fashion. In a preferred embodiment, there is incorporated a login filter that operative to ensure only the workflow items specific to the patients of the IDT provider who is logged into the system are displayed on the log. For instance, when the pharmacist logs into the application, only follow up items such as medication reconciliation or review assigned to the pharmacist for his/her patients will be displayed on the work log.

In addition to the patient's demographic information, the specific follow-up items pertaining to that IDT provider's workflow, the date of assignment, the follow-up date, and the individual staff member who assigned the follow-up item are displayed on the log. The user can "close" a specific follow-up item following its completion, subsequently removing the item from his/her workflow.

The patient specific workflow log integrated as part of the computer network, provides a complete list of all the outstanding follow-up items for that patient regardless of the IDT provider responsible. The patient specific workflow log is not limited by user login as described above, in order to facilitate improved communication between the IDT and care coordination for the patient. A sample computer screenshot of an inter disciplinary team assignment protocol is illustrated in FIG. 13.

Patient Education

Patient education is likewise extensively utilized in rendering care and is essential to bridge the gap in communication between providers and patients. Patient education also promotes compliance with care plans and in particular home-based care programs. The outcome is improved quality of care. The patient education program within the methods of the present invention has a fully integrated, nationally recognized third-party software with a wealth of disease-specific information in different languages. Specifically, according to preferred embodiments of the present invention, such educational materials are provided by Healthwise, Inc. of Boise, Idaho that provides over 3,000 unique patient educational materials for diseases, procedures and healthy lifestyle.

The program prescribes patient-specific education material, based on their gender, age, diagnoses and procedures (3 years of healthcare history). The program has the capability to order, track and trend patient-specific education that has been administered, giving the care coordinator complete control.

Prescriptive patient education is a patient specific program that prescribes education materials based on patient's condition and their demographic information; All education materials are ranked in the order in which it should be given to the patient. The prescriptive patient education consists of following sections:

a) Chronic Conditions/Problem Lists: This section list the patient's chronic conditions grouped according to HCC, using patients' diagnoses information with the latest diagnosed date (See FIG. 14).
  b) Surgical History: This section list the patient's surgical history, using procedure codes with the latest date when the procedure was performed (See FIG. 15).
  c) Patient education history: This section lists all the education materials that has been ordered as well as completed or imparted to the patient. It also displays who order the material and when was it given (See FIG. 16).
  d) Patient specific material recommended: This section list all the materials recommended for patients viewing or reading using patient's diagnoses, procedures, age, and gender. The recommended materials take into consideration the material that has not been ordered before (See FIG. 17).
  e) Order additional materials: This section enable users to order education material that are not in the recommended list (See FIG. 18).

Disease Management (DM)

The present invention further is operative to manage a variety of chronic diseases. In particular, the diseases targeted in the registries are the chronic conditions, medications that require management or incur high expense. These diseases are segregated for higher levels of review and for more careful implementation of care, whether in or outside the home environment. The disease management registry contains nine diseases as follow:

1) Anticoagulation
  2) Asthma
  3) Coronary Artery Disease (CAD)
  4) Congestive Heart Failure (CHF)
  5) Chronic Obstructive Pulmonary Disease (COPD)
  6) Depression
  7) Diabetes
  8) Hypertension
  9) Obstructive Sleep Apnea (OSA)

Disease management program consists of data that are made available for assessment and implementation of action items: i) Beneficiary Summary, ii) Enrollment rosters (nine rosters for each disease), iii) Enrollment call, iv) Disease management goal, and v) Follow-up roster. DM beneficiary summary page summarizes all pertinent information related to disease management for a specific patient. Enrollment rosters identify the list of patients to be enrolled into disease management programs. Enrollment call allows capturing communication with the patient regarding enrollment. Disease management goal page allows setting individual goal for each patient. Follow-up roster identify the list of task for each interdisciplinary team member.

Beneficiary Summary

This disease management summary page, shown in FIG. 19, contains patient specific information that includes a) the disease registries the patient should be enrolled into and monitored, b) the disease registries the patient is currently enrolled into, c) the disease registries criteria being monitored, the individual goal set and the latest values for each criteria, d) allows setting of follow up plans for inter disciplinary team members and e) lists the pending follow up items and ability to close them.

Enrollment Roster

There are nine enrollment rosters, one for each disease/condition discussed above. The enrollment rosters identify the list of potential patients to be enrolled into each disease registry. The list for each disease registry is generated using patient's conditions, laboratory data and medication information whereby the patient's conditions, laboratory data and medication information is associated with a point system, as discussed above. The criteria and point related to each criteria are displayed on the enrollment roster. The enrollment roster also includes a) whether the patient is a potential for complex case management with the tier b) the current enrollment status of the patient and c) results of the last call. FIG. 20 is an exemplary screenshot of a Diabetes Enrollment Page (when the details are collapsed). FIG. 21 is an exemplary screenshot of a Diabetes Enrollment Page (when the details are expanded).

Enrollment Call

The enrollment call page captures the pertinent information regarding the efforts to enroll the patient into disease management programs. The patient specific enrollment call page a) displays the potential disease management programs the patient should be enrolled b) allows the patient to be enrolled into disease management programs c) capture consent from the patient and details of the call. FIG. 22 depicts an exemplary enrollment call page.

Disease Management Goal

The disease management goal page allows setting of patient specific goals for each criteria, taking into consideration all the medical conditions of the patient. The goal page also includes the following a) last goals set for each criteria and b) previous values of each criteria as shown in FIG. 23.

A follow up roster creates a work list for interdisciplinary team members. The follow-up roster includes the following information a) patient to follow-up on; b) description for the follow up items; and c) the assigner of the follow up items as shown in FIG. 24.

A Trend Report provides a trend showing beneficiary's complexity assessment over a given period of time (See FIG. 25). It lists the complexity scores for each beneficiary, which can be sorted by the categories used to calculate the complexity score. Having a trend report helps the caregiver to know the well-being of the beneficiary whether his health condition is improving or deteriorating over time so appropriate measures can be taken.

Clicking on the Beneficiary ID gives the healthcare provider the individual scores for each category, which further opens the profile for that beneficiary, as of the date on which the evaluation was done, as illustrated in the exemplary screenshot of FIG. 26.

An Eligibility Verification Roster provides access to real-time admissions by integrating data from a third-party vendor that covers a wide geographic area. Case managers can reach out to patients admitted to a hospital to establish a relationship, fill out the hospital discharge and complexity profile forms in order to evaluate potential enrollment into the complex case management or disease management programs. A follow-up visit is then scheduled in order for the patient's aligned provider to review the patient's clinical data, address any outstanding quality care measures and manage the patient's overall health.

All the reports that can be generated pursuant to the methods of the present invention can be filtered by region, service area and network, or can be viewed at the company level using well-known data processing techniques. The advantage of this filtering system is that users can see how different operations are performing when compared to one another. It also makes it easier to identify outliers and quickly address problems that may exist only in certain geographies or regions. The present invention offers the capability to group several networks into service areas and analyze performance at the service area level.

In this regard, the entire user interface (UI) has been developed using open standards, such as JavaScript and HTML, to allow extendibility on mobile interfaces and platforms. The present invention works seamlessly on mobile platforms and devices such as the iPhone, iPad, Android and Windows mobile devices. Since the UI has been designed to work on mobile devices, the entire reporting capability that is available on desktops is available on mobile devices as well. Anything that can be accomplished on a desktop computer can be accomplished on a mobile version as well, as will be appreciated by those skilled in the art.

Likewise, in order to centrally administer access and rights to different providers, vendors, companies, and the like, the main login table is preferably hosted on the cloud (e.g., Microsoft SQL Azure). This allows the administrator to easily administer user rights without having to log into multiple applications that may be hosted on different servers. Any new settings made on the security setup workflow, automatically get pushed and replicated on the database servers. The whole security setup workflow is seamless and takes virtually no time for adding new users, modifying existing user roles or deleting users.

The above description is given by way of example, and not limitation. Given the above disclosure, one skilled in the art could devise variations that are within the scope and spirit of the invention disclosed herein, including various ways of administering healthcare to patients and in particular patients with chronic and complex conditions, that are exceptionally more efficient and effective that traditional "brick and mortar" based healthcare delivery. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for treating a patient suffering from an acute condition, the method comprising:
   providing at least one mobile device, comprising a network connection with internet access, loaded with, and operable to run, video teleconferencing software;
   providing a plurality of databases, located on a plurality of servers connected to the network, the plurality of databases being located in a plurality of facilities comprising dialysis centers, facilities for performing radiology, and laboratory facilities;
   providing a central database, stored on at least one server, the central database in communication, with the plurality of databases;
   transferring data from the plurality of databases to the central database;
   transforming the data from the plurality of databases into a patient file corresponding to the patient, wherein the central database is adapted to be routinely updated, by the plurality of databases, to provide up-to-date information for the patient;
   determining, by at least one complex case management application in communication with the central database, implemented on the at least one server, and accessible by the mobile device, whether the patient is afflicted with a complex medical condition, and, if so, placing the patient in to a complex care management regime, said complex medical condition defined by:
      three or more chronic medical conditions selected from the group consisting of asthma, congestive heart failure, chronic obstructive pulmonary disease, diabetes, obesity, AIDS/HIV, anticoagulation, hypertension, peripheral artery disease, coronary artery disease, end-stage renal disease, and chronic kidney disease, and one high risk criteria selected from the group consisting of poor social support, poor functional status, poor nutritional status, two or more hospitalizations in the preceding twelve months, and three or more emergency room visits in the preceding twelve months; or
      a predetermined range of complexity scores calculated by a scoring module of the at least one complex case management application, the at least one complex case management application assigning points based on criteria including:
         demographic information including the patient's age, sex, and residence, the residence selected from the group consisting of home, assisted living, skilled nursing facility, and board and care facility;
         total number of ER visits and hospital admissions in the last six months;
         major organ system dysfunction including cardiovascular, respiratory, renal, nervous system, hematology/oncology, digestive, urinary, infectious disease, endocrine, and musculoskeletal;
         total number of drug classifications;
         overall functional status including functional limitations; and
         support network including social support and caregiver network;
   displaying, on the mobile device, a plurality of screens of a user interface operable in the at least one complex case management application and implemented using Hyper Text Markup Language and/or JavaScript, the plurality of screens including selected data from the patient file, the plurality of screens including:
      a summary page including demographic information, a clinical profile, support network information, and links to at least two other screens of the plurality of screens;
      a complex case management complexity profile accessible through one of the links on the summary page, the complex case management complexity profile including residence information, the number of ER visits and hospital admissions in the last six months, a major organ failure section, the total number of drug classifications currently prescribed for the patient, a listing of the drug classifications, a functional status summary, a listing of limitations regarding functional status, a summary of the patient's support network, and a complexity score;
      a chronic conditions list;
      a disease management member summary including actions taken, follow-up plans, and open items; and
      a complexity profile report and trend including patient name and complexity scores over time;
   providing at least one remote computer terminal linked to the at least one mobile device, the at least one remote computer terminal loaded with, and operable to run, the video teleconferencing software, the at least one remote computer terminal operative to provide direct, real time communication with a healthcare professional operating the mobile device;
   providing a cloud-hosted main login table of an access management application, the access management application implemented on the at least one server, the main login table separately hosted from the access management application, the main login table, through the access management application limiting healthcare provider access in the disease management member summary screen of the user interface to open items that the healthcare provider has rights to close out;
   if the patient is determined to be afflicted with a complex medical condition, granting access to the patient to initiate a request for care concerning the acute condition using the video teleconferencing software on the at least one remote computer terminal, displaying, on the mobile device, the video teleconference and simultaneously displaying the user interface regarding the patient, wherein the at least one application is configured to access the patient file stored in the central database, determining, based on a combination of the video teleconference and the patient file, whether home-based treatment of the patient is appropriate for the acute condition, and, depending on the result, either treating the patient for the acute condition in a home setting with home-based medical equipment or treating the patient for the acute condition in a medical facility; and,
   if the patient is determined not to be afflicted with a complex medical condition, treating the patient for the acute condition in a medical facility without a determination using the video teleconferencing software as to whether home-based treatment of the patient is appropriate for the acute condition.

* * * * *